United States Patent
Leow et al.

(10) Patent No.: US 9,931,368 B2
(45) Date of Patent: Apr. 3, 2018

(54) ANTI-OBESITY AND ANTI-DYSLIPIDEMIC EFFECTS OF OIL PALM PHENOLICS IN TREATING ATHEROSCLEROSIS AND CARDIOVASCULAR DISEASE

(71) Applicant: Malaysian Palm Oil Board, Kajang (MY)

(72) Inventors: Soon Sen Leow, Kajang (MY); Ravigadevi Sambanthamurthi, Petaling Jaya (MY); Yew Ai Tan, Kuala Lumpur (MY); Kalyana Sundram P. Manickam, Petaling Jaya (MY); Mohd Basri Wahid, Batu Caves (MY)

(73) Assignee: Malaysian Palm Oil Board, Kajang, Selangor (MY)

( * ) Notice: Subject to any disclaimer, the term of this patent is extended or adjusted under 35 U.S.C. 154(b) by 0 days.

(21) Appl. No.: 14/531,731

(22) Filed: Nov. 3, 2014

(65) Prior Publication Data

US 2015/0164969 A1    Jun. 18, 2015

Related U.S. Application Data

(63) Continuation of application No. 13/521,055, filed as application No. PCT/MY2011/000002 on Jan. 7, 2011, now abandoned.

(30) Foreign Application Priority Data

Jan. 7, 2010   (MY) .......................... PI 2010000060

(51) Int. Cl.
  *A61K 36/889*   (2006.01)
  *A61K 31/05*    (2006.01)

(52) U.S. Cl.
  CPC ............ *A61K 36/889* (2013.01); *A61K 31/05* (2013.01)

(58) Field of Classification Search
  CPC .................................................... A61K 36/889
  USPC ................................................. 424/727, 774
  See application file for complete search history.

(56) References Cited

U.S. PATENT DOCUMENTS

| | | | |
|---|---|---|---|
| 7,387,802 B2 | 6/2008 | Sambanthamurthi et al. | |
| 2006/0024390 A1 | 2/2006 | Schauss et al. | |
| 2011/0003019 A1* | 1/2011 | Mohamed ............. | A23L 1/3002 424/727 |

* cited by examiner

*Primary Examiner* — Christopher R Tate
*Assistant Examiner* — Deborah A Davis
(74) *Attorney, Agent, or Firm* — Merchant & Gould P.C.

(57) ABSTRACT

A composition comprising extracts containing oil palm phenolics in an amount effective for use in a method of reducing cholesterol biosynthesis and thus preventing obesity. The composition up regulates fatty acid beta oxidation and down regulates cholesterol biosynthesis in livers. The composition is useful for prevention of obesity associated diseases. The composition delays the onset of obesity and attenuates the inflammatory response of atherogenic diet, whereby the composition aids to suppress the inflammatory response thereby ameliorating artherosclerosis. The composition delays weight gain or obesity thereby preventing the effects of dyslipidemia.

10 Claims, 21 Drawing Sheets

ANTI-OBESITY AND ANTI-DYSLIPIDEMIC EFFECTS OF OIL PALM PHENOLICS IN TREATING ATHEROSCLEROSIS AND CARDIOVASCULAR DISEASE

CLAIM OF PRIORITY

This application is a continuation of U.S. application Ser. No. 13/521,055, filed on Mar. 15, 2013, which is a National Phase application of International Application No.: PCT/MY2011/000002, filed on Jan. 7, 2011, which claims priority to Malaysian Patent Application No. PI2010000060, filed on Jan. 7, 2010, which are hereby incorporated by reference in their entirety.

FIELD OF THE INVENTION

The present invention provides a method of delaying weight gain or obesity and preventing the effects of dyslipidemia caused by an atherogenic diet in an animal. It comprises the step of administering oil palm phenolics in the drinking water to said animal. The aforementioned properties of oil palm phenolics are attributed to the up-regulation of fatty acid beta oxidation and down-regulation of cholesterol biosynthesis in the liver, when the said animal was given a low-fat normal diet. In addition, oil palm phenolics also up-regulated unfolded protein response in the liver, down-regulated antigen presentation and processing in the spleen as well as up-regulated antioxidant genes in the heart, when the said animal was given a high-fat, cholesterol-containing, atherogenic diet. Oil palm phenolics may thus confer anti-inflammatory and antioxidative effects for the prevention of atherosclerosis and cardiovascular disease.

BACKGROUND OF THE INVENTION

Cardiovascular disease, together with atherosclerosis, is the first cause of death in the world. A variety of risk factors are known to be associated with the pathogenesis of atherosclerosis and cardiovascular disease. These factors include hypercholesterolemia, hyperlipidemia, hyperglycemia, hypertension, obesity, elevated levels of plasma homocysteine and hemostatic factors, family history, the male gender, stress, smoking, lack of exercise, high-fat diets, infectious agents and aging. People with diabetes usually have more severe debility from atherosclerotic events over time than non-diabetics.

Atherosclerosis is a disease affecting arterial blood vessels, and it involves the hardening (calcification) of arteries and the formation of atheromatous plaques within the arteries. As with other chronic diseases, atherosclerosis is believed to be caused by the accumulation of harmful free radicals and reactive oxygen species in the body. It is associated with systemic immune responses and inflammation. Atherosclerosis causes two main problems, infarction (complete coronary occlusion) and aneurysm (partial coronary occlusion), and it can actually be viewed as a problem of wound healing and chronic inflammation. Atheroslerosis may cause brain strokes, heart attacks and peripheral artery occlusive diseases in the lower extremities.

The pathophysiology of atherosclerosis comprises various important steps, including enhanced endothelial focal adhesiveness, permeability and pro-coagulation (endothelial dysfunction), expression of adhesion molecules, monocyte adhesion and immigration, formation of foam cell and fatty streaks, smooth muscle cell (SMC) migration from the tunica media into the tunica intima, plaque formation and finally, plaque rupture and thrombus formation. A prevalent theme in atherosclerosis is thus the presence of oxidative stress and inflammation, due to the oxidation of LDL.

The oxidation of low-density lipoprotein (LDL) has been accepted as an important initial event in the development of atherosclerosis. Reactive oxygen species can stimulate the oxidation of LDL, and oxidized LDL which is not recognized by the LDL receptor is then taken up by scavenger receptors in macrophages leading to foam cell formation and atheromatous plaques. In addition, macrophages also possess toll-like receptors which bind pathogen-like molecules and initiate a signalling cascade which leads to cell activation. These macrophages produce inflammatory cytokines, chemokines, free radicals, growth-regulating molecules, metalloproteinases and other hydrolytic enzymes. Apoptosis of foam cells, which is influenced by cytokine expression and the macrophage activation state also contributes to the formation of a necrotic core.

Previous studies show that among the genes which have increased expression in the atherosclerotic vessel wall are those involved in inflammation, such as chemokine and chemokine receptors, interleukin and interleukin receptors, major histocompatibility complex (MHC) molecules, endothelial cell adhesion molecules, extracellular matrix and matrix remodeling proteins, matrix metalloproteinase genes, transcription factors, lipid metabolism and vascular calcification genes, as well as macrophages and smooth muscle cell specific genes. On the other hand, among the genes with decreased expression in the atherosclerotic vessel wall include anti-adhesive, anti-proliferative and anti-inflammatory genes as well as differentiated muscle markers.

Besides surgical interventions such as angioplasty and bypass surgery, various pharmacological interventions have been used for the treatment of atherosclerosis and the associated cardiovascular disease. Medications to lower cholesterol and LDL as well as those which increase high-density lipoprotein (HDL) are normally utilized to prevent the occurrence of atherosclerosis. For example, statins are used to inhibit an enzyme called Hmgcr (3-hydroxy-3-methylglutaryl-coenzyme-A reductase), which is involved in cholesterol biosynthesis. Yet another therapeutic strategy in the treatment of atherosclerosis is the use of cell cycle inhibitors which include pharmacological agents, irradiation or gene therapy, as vascular proliferation is central to atherosclerosis.

Immunosuppressive and anti-inflammatory drugs such as cyclosporine which block the activation of T cells may also be used as a therapeutic treatment for atherosclerosis. In addition to its cholesterol-lowering properties, statins also show pleiotropic effects including immunosuppressive properties. Vaccination with oxidized LDL, bacteria containing modified phospholipids or heat shock proteins is also an attractive approach to induce protective immunity against atherosclerosis. Yet other approaches include transfer of anti-inflammatory interleukins and administration of decoys and antibodies directed against pro-inflammatory interleukins.

Most of the current approaches however, aim to treat atherosclerosis rather than to prevent it. With the increase in health awareness among the public, it was realized through epidemiological and experimental studies that diets containing high amount of phytochemicals can also provide protection against free radical-induced diseases such as atherosclerosis and cardiovascular disease, due to their high antioxidant activities. For example, dietary antioxidants such as vitamin E, vitamin C, carotenoids, polyphenols and coenzyme Q10 were found to be able to prevent atherogenesis.

Phenolic antioxidants from soy, pomegranate, ginger and red wine were also found to attenuate atherosclerosis either by LDL-dependent mechanisms such as reducing LDL levels, inhibiting LDL oxidation and increasing the antioxidant status or via other LDL-independent mechanisms. Resveratrol, a phenolic phytoalexin found in red wine, was also suggested to mediate cardioprotection through the preconditioning effect, rather than direct protection. Preconditioning is achieved by subjecting the heart to a therapeutic amount of stress, thereby disturbing normal cardiovascular homeostasis and reestablishing a modified homeostatic condition with increased cardiac defences that can withstand subsequent stress insults. Resveratrol was also found to increase the lifespan and survival of mice on a high-calorie diet. Plant phenolics are thus promising candidates for the prevention of atherosclerosis and related cardiovascular disease.

The oil palm (Elaeis guineensis) contains various phytochemicals which possess significant antioxidant properties such as carotenoids, tocopherols and tocotrienols. The extraction of water-soluble phenolics from the palm oil mill effluent (POME) through a completely solvent-free process recovers another type of antioxidant from the oil palm, designated the Essence of Palm® which contains various phenolic acids and polyphenols. This discovery potentiates the two-pronged approach of reducing environment pollution caused by POME while producing premium products for the pharmaceutical, nutraceutical and cosmeceutical markets. Oil palm phenolics showed significant biological activities against LDL oxidation, increased the amounts of HDL in hamsters fed an atherogenic diet and attenuated atherosclerosis in blood vessels of atherogenic diet-fed rabbits.

In this study, we extended the knowledge that oil palm phenolics can attenuate atherosclerosis by hypothesizing that the extract might influence certain gene expression changes. We thus tested this hypothesis by feeding mice with either a low-fat normal diet (14.6% kcal/kcal energy) or a high-fat (40.5% kcal/kcal energy) atherogenic diet containing cholesterol (0.15% w/w). Each group was further given either distilled water (control group) or oil palm phenolics (treatment group). By harvesting major organs such as livers, spleens and hearts for microarray gene expression profiling analysis, we identified the biological changes caused by oil palm phenolics in the normal diet fed mice, by the atherogenic diet and by oil palm phenolics in the atherogenic diet fed mice, as well as discovered how the extract changed the gene expression profiles caused by the atherogenic diet.

SUMMARY OF THE INVENTION

The invention relates to a composition useful for providing anti-obesity or anti-dyslipidemics properties, and thus the prevention of artherosclerosis and cardiovascular diseases related thereto.

BRIEF DESCRIPTION OF THE DRAWINGS

FIG. 14A relates specifically to TP-FCR; FIG. 14B relates specifically to FRAP; FIG. 14C relates specifically to DPPH; and FIG. 14D relates specifically to TEAC. # identifies those samples for which $p<0.05$ vs. Normal Diet+Distilled Water; n=6. Error bars indicate S.E.M.

DETAILED DESCRIPTION

All male inbred BALB/c mice (n=40) which were designated for this study were purchased from the Institute of Medical Research, Kuala Lumpur, Malaysia, at around five weeks of age just after weaning. All animal procedures were approved by the Animal Care and Use Committee of the University of Malaya, Kuala Lumpur, Malaysia. The animals were randomly assigned into cages (n=5 per cage) and acclimatized for one week, during which a standard chow diet purchased from the University of Malaya, and distilled water were given. At the start of the experiment, the diet of the animals was changed to a custom-made low-fat normal diet (58.2% kcal/kcal carbohydrate, 27.2% kcal/kcal protein and 14.6% kcal/kcal fat, including cellulose, mineral mix, vitamin mix and DL-methonine) or a custom-made high-fat atherogenic diet (40.5% kcal/kcal carbohydrate, 19.0% kcal/kcal protein and 40.5% kcal/kcal fat, including 0.15% w/w cholesterol, as well as cellulose, mineral mix, vitamin mix and DL-methonine). The normal control group (n=10) and the atherogenic control group (n=10) were supplemented with distilled water while the normal treatment group (n=10) and the atherogenic treatment group (n=10) were supplemented with oil palm phenolics as drinks ad libitum. The antioxidant content of the oil palm phenolics given was around 1500 ppm gallic acid equivalent. Food and fluid were changed daily. During the animal feeding process, body weights were monitored every week. After six weeks, the mice were sacrificed via euthanasia with diethyl ether and blood samples were collected via cardiac puncture. Six major organs including livers, spleens, hearts, kidneys, lungs and brains were excised, blotted, weighed, snap-frozen in liquid nitrogen and stored at −80° C.

Figure 1A:
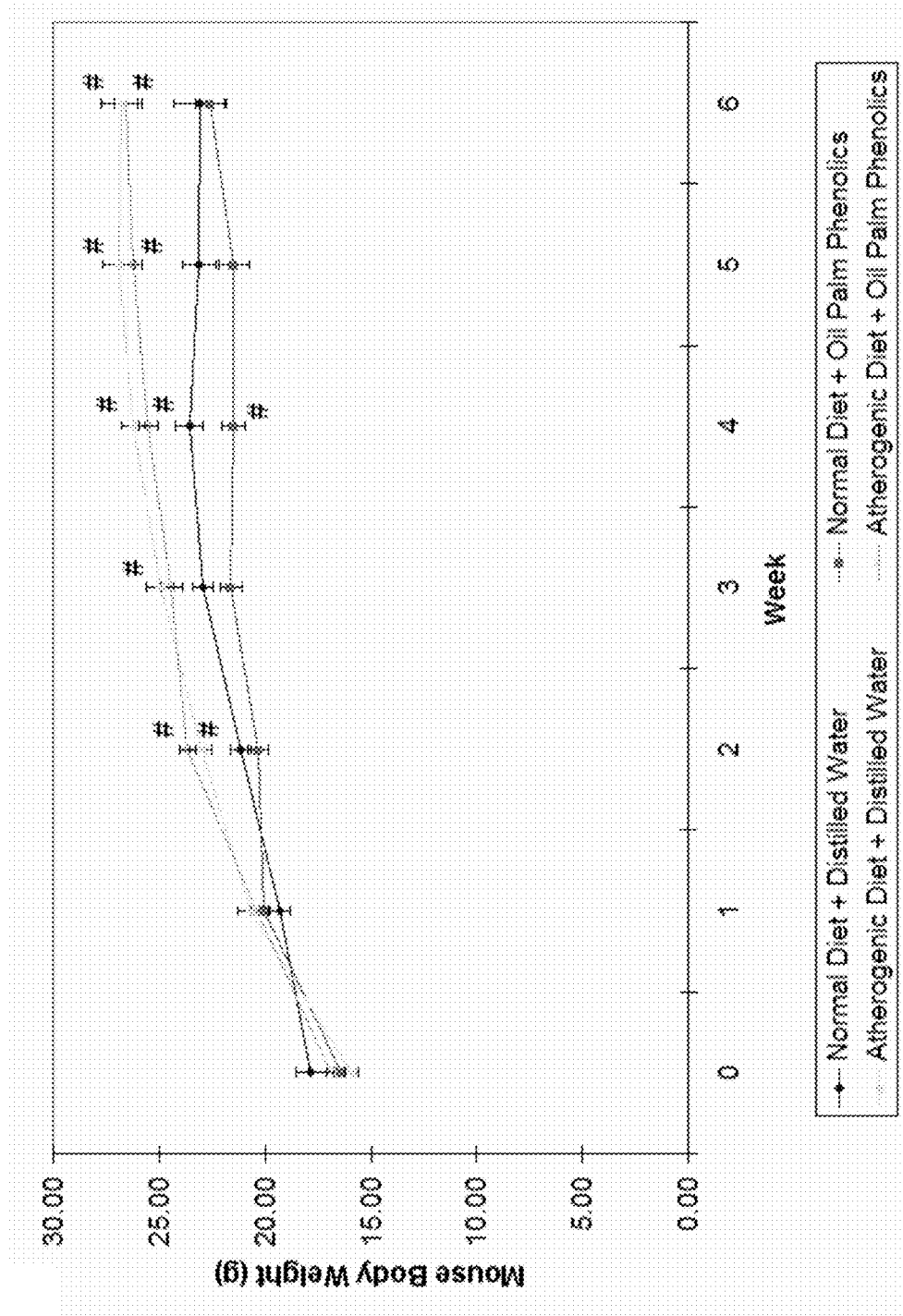
FIG. 1A shows a graph for body weights of mice.
Figure 1B:
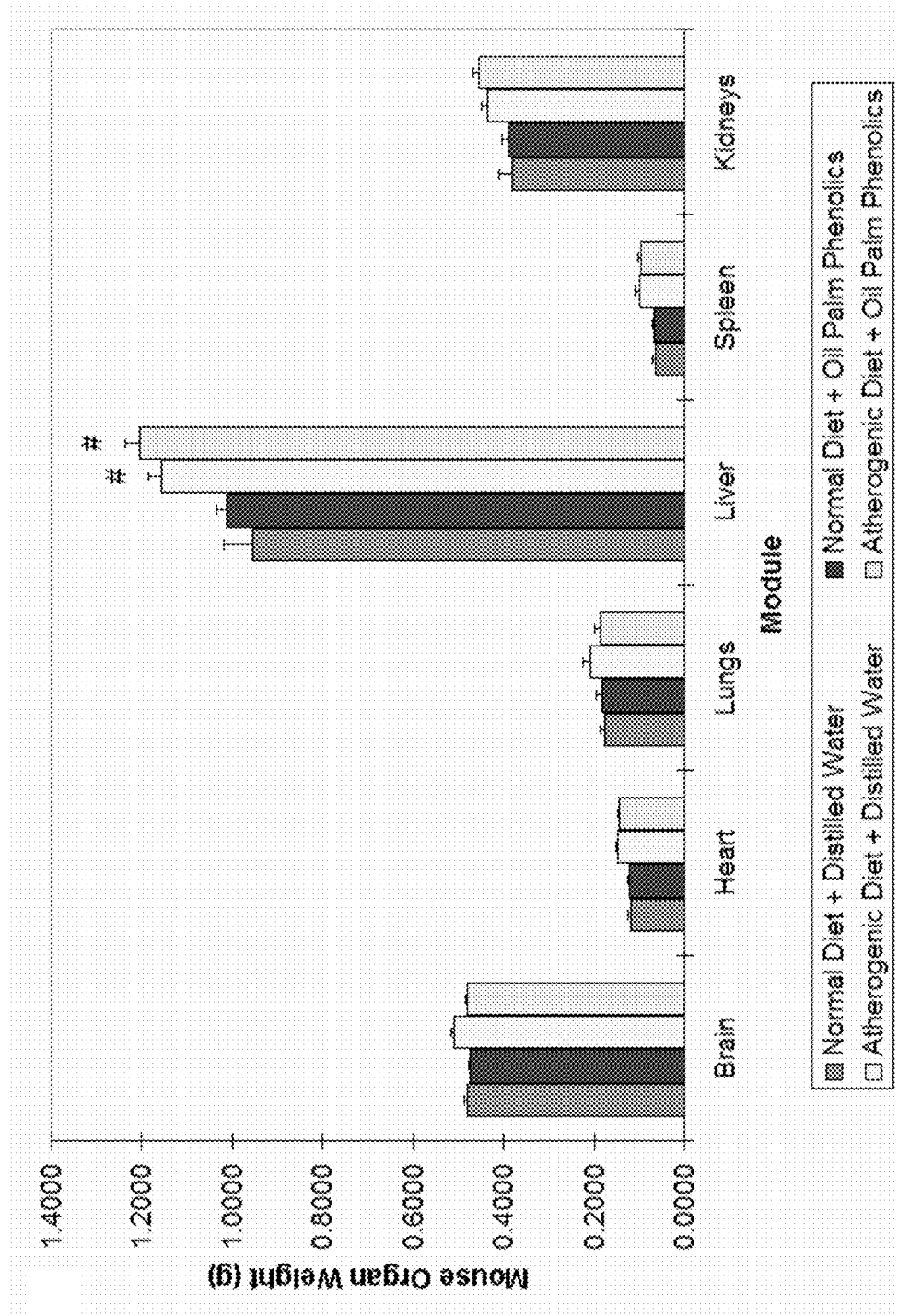
FIG. 1B shows a graph of organ weights of mice treated with (1) normal diet+distilled water; (2) normal diet+oil palm phenolics; (3) atherogenic diet+distilled water; and (4) atherogenic diet+oil palm phenolics. The data points marked with # represent $p<0.05$ vs. Normal Diet+Distilled Water; n=10. Error bars indicate S.E.M.

The body weights of mice steadily increased every week throughout the six weeks of feeding, with those on the atherogenic diet showing a higher increase in weight gain compared to those on the normal diet (FIG. 1A). In contrast, mice in the normal treatment group showed a delay in weight gain throughout the six weeks of feeding (FIG. 1A). When the organ weights from the animals were compared, the atherogenic diet was found to cause an increase in the weight of mouse livers (FIG. 1B). On the other hand, oil palm phenolics did not significantly affect organ weights, both in mice given the normal diet and the atherogenic diet (FIG. 1B). These results indicate that the addition of extra fat and cholesterol in the atherogenic diet increased its energy content. This caused the livers of mice in the two atherogenic diet groups to enlarge in order to accommodate an increased need for fat and cholesterol processing, and resulted in a higher weight gain.

A portion (200 μL) of whole blood samples obtained from about half of the animals (n=4) was aliquoted into a tube containing ethylenediaminetetraacetic acid (EDTA) (Ambion, Austin, Tex.) to prevent clotting. These whole blood samples were immediately sent after dissection of the animals to the Clinical Biochemistry and Hematology Laboratory, Department of Veterinary Pathology and Microbiology, Faculty of Veterinary Medicine, University of Putra Malaysia (UPM), Serdang, Selangor, Malaysia, for hematology analysis. The analysis was carried out using the Animal Blood Counter Vet Hematology Analyzer (Horiba ABX, France).

In order to obtain sera, the remaining blood samples from all of the animals (n=10) were allowed to clot at room temperature for 2 hours before centrifuging them at 3300 rpm for 5 minutes, after which the supernatant layers were collected and stored at −20° C. A portion (100 μL) of each serum sample (n=6 per group) was kept in aliquots for cytokine profiling and antioxidant analysis. The remaining serum samples (around 200 μL per replicate) were then sent for clinical biochemistry analysis using the Roche/Hitachi 902 Chemistry Analyzer (Roche/Hitachi, Switzerland) in the Clinical Biochemistry and Hematology Laboratory, Department of Veterinary Pathology and Microbiology, Faculty of Veterinary Medicine, UPM. Clinical biochemistry parameters which were examined include alanine aminotransferase, aspartate aminotransferase, glucose, serum total protein, albumin, globulin, albumin:globulin ratio, total cholesterol, triglycerides, low-density lipoprotein (LDL) and high-density lipoprotein (HDL). Two samples in each control group and three samples in each treatment group were excluded from data analysis due to blood lysis.

In terms of hematology, mice given the atherogenic diet showed a significant increase in the levels of white blood cells, neutrophils and lymphocytes when compared to those given the normal diet (Table 1), indicating the presence of an inflammatory response. Oil palm phenolics did not affect hematology parameters in both modules (Table 1). In terms of clinical biochemistry, significant changes caused by the atherogenic diet involved the levels of glucose (↓), albumin (↓), globulin (↑), A:G (↓), total cholesterol (↑), LDL-C(↑) and HDL-C(↑) (Table 2). Oil palm phenolics did not cause significant changes in the clinical biochemistry parameters measured in each module, except for normalizing glucose levels in the atherogenic diet module (Table 2).

TABLE 1

Hematology Parameters Measured Using Mouse Whole Blood Samples

| Test | Normal Diet + Distilled Water | Normal Diet + Oil Palm Phenolics | Atherogenic Diet + Distilled Water | Atherogenic Diet + Oil Palm Phenolics |
|---|---|---|---|---|
| Red Blood Cells ($\times 10^{12}$/L) | 9.93 ± 0.32 [a] | 10.15 ± 0.12 [a] | 10.08 ± 0.21 [a] | 10.02 ± 0.08 [a] |
| Hemoglobin (g/L) | 148 ± 4 [a] | 149 ± 1 [a] | 149 ± 3 [a] | 149 ± 1 [a] |
| Hematocrit/Packed Cell Volume (L/L) | 0.40 ± 0.01 [a] | 0.40 ± 0.00 [a] | 0.40 ± 0.02 [a] | 0.40 ± 0.00 [a] |
| Mean Corpuscular Volume (fL) | 41 ± 1 [a] | 40 ± 0 [a] | 40 ± 1 [a] | 40 ± 1 [a] |
| Mean Corpuscular Hemoglobin Concentration (g/L) | 369 ± 6 [a] | 373 ± 4 [a] | 373 ± 7 [a] | 372 ± 5 [a] |
| White Blood Cells ($\times 10^9$/L) | 2.0 ± 0.6 [a] | 1.5 ± 0.3 [a] | 3.3 ± 0.3 [b] | 3.0 ± 0.1 [b] |
| B Neutrophils ($\times 10^9$/L) | 0.05 ± 0.01 [a] | 0.04 ± 0.01 [a] | 0.10 ± 0.02 [b] | 0.10 ± 0.02 [b] |
| S Neutrophils ($\times 10^9$/L) | 0.48 ± 0.17 [a] | 0.35 ± 0.09 [a] | 0.83 ± 0.07 [b] | 0.77 ± 0.06 [b] |
| Lymphocytes ($\times 10^9$/L) | 1.36 ± 0.38 [a] | 1.01 ± 0.20 [a] | 2.06 ± 0.22 [b] | 1.99 ± 0.17 [b] |
| Monocytes ($\times 10^9$/L) | 0.09 ± 0.02 [a] | 0.07 ± 0.02 [a] | 0.08 ± 0.04 [a] | 0.09 ± 0.03 [a] |
| Eosinophils ($\times 10^9$/L) | 0.03 ± 0.01 [a] | 0.01 ± 0.00 [a] | 0.06 ± 0.02 [a] | 0.06 ± 0.03 [a] |
| Basophils ($\times 10^9$/L) | 0.00 ± 0.00 [a] | 0.00 ± 0.00 [a] | 0.00 ± 0.00 [a] | 0.00 ± 0.00 [a] |
| Thrombocytes ($\times 10^9$/L) | 533 ± 111 [a] | 621 ± 103 [a] | 644 ± 37 [a] | 619 ± 21 [a] |
| P Prothrombin (g/L) | 79 ± 2 [a] | 80 ± 1 [a] | 78 ± 2 [a] | 79 ± 2 [a] |

Values shown are Means ± S.E.M.;
Means with different superscript letters are significantly different ($P < 0.05$).

TABLE 2

Clinical Biochemistry Parameters Measured Using Mouse Serum Samples

| Test | Normal Diet + Distilled Water | Normal Diet + Oil Palm Phenolics | Atherogenic Diet + Distilled Water | Atherogenic Diet + Oil Palm Phenolics |
|---|---|---|---|---|
| Alanine Aminotransferase (ALT) (U/L) | 34.4 ± 3.3 $^a$ | 42.5 ± 6.5 $^a$ | 41.8 ± 10.7 $^a$ | 32.2 ± 5.1 $^a$ |
| Aspartate Aminotransferase (AST) (U/L) | 175.2 ± 23.8 $^a$ | 240.4 ± 22.3 $^a$ | 174.8 ± 29.3 $^a$ | 157.2 ± 32.2 $^a$ |
| Glucose (mmol/L) | 6.0 ± 1.1 $^a$ | 6.7 ± 0.4 $^a$ | 5.3 ± 0.4 $^{a,b}$ | 7.4 ± 0.4 $^{a,c}$ |
| Serum Total Protein (g/L) | 53.8 ± 1.8 $^a$ | 53.8 ± 1.1 $^a$ | 53.2 ± 0.9 $^a$ | 54.8 ± 0.7 $^a$ |
| Albumin (g/L) | 34.0 ± 0.9 $^a$ | 33.1 ± 1.3 $^a$ | 29.4 ± 0.7 $^b$ | 31.0 ± 0.7 $^b$ |
| Globulin (g/L) | 19.8 ± 1.1 $^a$ | 20.8 ± 0.8 $^a$ | 23.8 ± 0.7 $^b$ | 23.7 ± 0.7 $^b$ |
| A:G | 1.8 ± 0.1 $^a$ | 1.6 ± 0.1 $^a$ | 1.2 ± 0.1 $^b$ | 1.3 ± 0.1 $^b$ |
| Total Cholesterol (mmol/L) | 3.46 ± 0.13 $^a$ | 3.53 ± 0.19 $^a$ | 4.77 ± 0.15 $^b$ | 4.76 ± 0.19 $^b$ |
| Triglycerides (mmol/L) | 1.05 ± 0.08 $^a$ | 1.04 ± 0.11 $^a$ | 1.13 ± 0.04 $^a$ | 1.14 ± 0.15 $^a$ |
| Low-Density Lipoprotein (mmol/L) | 0.15 ± 0.02 $^a$ | 0.18 ± 0.03 $^a$ | 0.26 ± 0.03 $^b$ | 0.30 ± 0.06 $^b$ |
| High-Density Lipoprotein (mmol/L) | 2.79 ± 0.11 $^a$ | 2.83 ± 0.17 $^a$ | 4.05 ± 0.11 $^b$ | 3.93 ± 0.14 $^b$ |

Values shown are Means ± S.E.M.;
Means with different superscript letters are significantly different ($P < 0.05$).

Microarray Gene Expression Analysis

For gene expression analysis, livers from the normal diet module as well as livers, spleens and hearts from the atherogenic diet module were used in the total RNA extraction process. Total RNA isolation from mouse organs was carried out using the RNeasy Mini Kit (Qiagen, Inc., Valencia, Calif.) and QIAshredder homogenizer (Qiagen, Inc., Valencia, Calif.). The total RNA samples obtained were subjected to NanoDrop 1000A Spectrophotometer for yield and purity assessment. Integrity of the total RNA samples was then assessed using the Agilent 2100 Bioanalyzer (Agilent Technologies, Palo Alto, Calif.) and Agilent RNA 6000 Nano Chip Assay Kit (Agilent Technologies, Palo Alto, Calif.). Four total RNA samples with the highest RNA Integrity Numbers and 28S/18S rRNA ratios within each condition were then selected for microarray studies.

Amplification of total RNA samples which were of high yield, purity and integrity was carried out using the Illumina TotalPrep RNA Amplification Kit (Ambion, Inc., Austin, Tex.). The cRNA produced was then hybridized to the Illumina MouseRef-8 Expression BeadChip Version 1 (Illumina, Inc., San Diego, Calif.), using the Direct Hybridization Kit (Illumina, Inc., San Diego, Calif.). Illumina MouseRef-8 Expression BeadChips contained 50-mer gene-specific probes for over 24000 genes which were designed based on the Mouse Exonic Evidence Based Oligonucleotide (MEEBO) set, the RIKEN FANTOM 2 database and the National Center for Biotechnology Information (NCBI) RefSeq (Release 5) transcript database. Microarray hybridization, washing and scanning were carried out according to the manufacturer's instructions.

In brief, cRNA was added with a hybridization buffer, and the hybridization mixture was then briefly heated and hybridized to an Illumina BeadChip. The hybridized microarray then underwent a series of washes using the wash buffers provided and 100% ethanol (Merck, Darmstadt, Germany). Non-specific hybridization was blocked before incubating the microarray with the Amersham Fluorolink Streptavidin Cy-3 dye (GE Healthcare Bio-Sciences, Little Chalfont, UK) for detection, followed by a final wash with the wash buffer. The microarray was then dried and scanned with the Illumina BeadArray Reader confocal scanner and Illumina BeadScan software (Illumina, Inc., San Diego, Calif.), available at the Malaysia Genome Institute, National University of Malaysia.

Quality control of the hybridization, microarray data extraction and initial analysis were carried out using the Illumina BeadStudio software (Illumina, Inc., San Diego, Calif.). Outlier samples were removed via hierarchical clustering analysis provided by the Illumina BeadStudio software and also using the TIGR MeV software, via different distance metrics. A minimum of three replicates per condition (with outliers removed) was then considered for further analysis.

It should be noted that four comparisons of the microarray data obtained were made in this study, with the first comparison to find out gene expression changes caused by oil palm phenolics in the normal diet module (Normal Diet+Oil Palm Phenolics: Normal Diet+Distilled Water). The second comparison was made to find out gene expression changes caused by the atherogenic diet (Atherogenic Diet+Distilled Water: Normal Diet+Distilled Water). The third comparison was made to identify gene expression changes caused by oil palm phenolics in the atherogenic diet module (Atherogenic Diet+Oil Palm Phenolics: Atherogenic Diet+Distilled Water). The fourth comparison was carried out to identify genes which were regulated differently by the atherogenic diet and oil palm phenolics, by comparing results from the second and third comparison. The first three comparisons were carried out separately before the fourth comparison was made.

For the first three comparisons, gene expression values were normalized using the rank invariant method and genes which had a Detection Level of more than 0.99 in either condition (control or treatment) were considered significantly detected. To filter the data for genes which changed significantly in terms of statistics, the Illumina Custom error model was used and genes were considered significantly changed at a |Differential Score| of more than 20, which was equivalent to a P Value of less than 0.01. The stringency of this filtering criterion was lowered to a |Differential Score| of more than 13, which was equivalent to a P Value of less than 0.05, should less than 100 genes were considered significantly changed. Since the results of this statistical analysis would be used for functional analysis, it would be relevant to include more genes by using a lower threshold to give statistical power to the functional analysis, in which functional significance could be assessed.

The genes and their corresponding data were then exported into the Microsoft Excel software for further analysis. To calculate fold changes, an arbitrary value of 10 was given to expression values which were less than 10. Fold changes were then calculated by dividing means of Signal Y (treatment) with means of Signal X (control) if the genes were up-regulated and vice versa if the genes were down-regulated. Two-way (gene and sample) hierarchical clustering of the significant genes was then performed using the TIGR MeV software to ensure that the replicates of each condition were clustered to each other. The Euclidean distance metric and average linkage method were used to carry out the hierarchical clustering analysis.

For the first three comparisons, changes in biological pathways and gene ontologies were also assessed via functional analysis, using the GenMAPP and MAPPFinder softwares. The MAPPFinder software ranks GenMAPPs (pathways) and gene ontologies based on hypergeometric distribution. GenMAPPs and gene ontologies which had Permuted P Values of less than 0.01, Numbers of Genes Changed of more than or equal to 2 and Z Scores of more than 2 were considered significant. A Permuted P Value of less than 0.05 was used when genes were selected using a |Differential Score| of more than 13, in order to identify more GenMAPPs and gene ontologies affected.

It should be noted that the MAPPFinder software clusters multiple probes for a distinct gene into a single gene grouping in order to calculate the number of distinct genes which meet the user-defined criteria, not the probes. In this study, up- and down-regulated genes were analyzed separately in the functional enrichment analysis but were viewed together in each GenMAPP. Boxes coloured yellow indicate genes which were up-regulated while those coloured blue indicate genes which were down-regulated. The fold changes are indicated next to the boxes. Individual boxes which have different shadings within them indicate the presence of multiple probes (splice transcripts) within a single gene.

Changes in regulatory networks were also analyzed through the use of Ingenuity Pathways Analysis software (Ingenuity® Systems, Redwood City, Calif.) [36] for the first three comparisons. A data set containing differentially expressed genes and their corresponding fold changes was uploaded into the application. Analysis of up- and down-regulated genes were carried out separately. Each gene identifier was mapped to its corresponding gene object in the Ingenuity Pathways Knowledge Base. These genes were overlaid onto a global molecular network developed from information contained in the Ingenuity Pathways Knowledge Base. Networks of these focus genes were then algorithmically generated based on their connectivity.

A network is a graphical representation of the molecular relationships between genes or gene products. Genes or gene products were represented as nodes, and the biological relationship between two nodes was represented as an edge (line). The intensity of the node color indicates the degree of up- (red) or down- (green) regulation. Nodes were displayed using various shapes that represented the functional class of the gene product. Edges were displayed with various labels that described the nature of the relationship between the nodes. Gene descriptions which were not referenced emanated directly from the Ingenuity Pathways Analysis software.

Oil Palm Phenolics Up-Regulated Fatty Acid Beta Oxidation Genes and Down-Regulated Cholesterol Biosynthesis Genes in the Liver (Normal Diet Module)

Figure 2A:
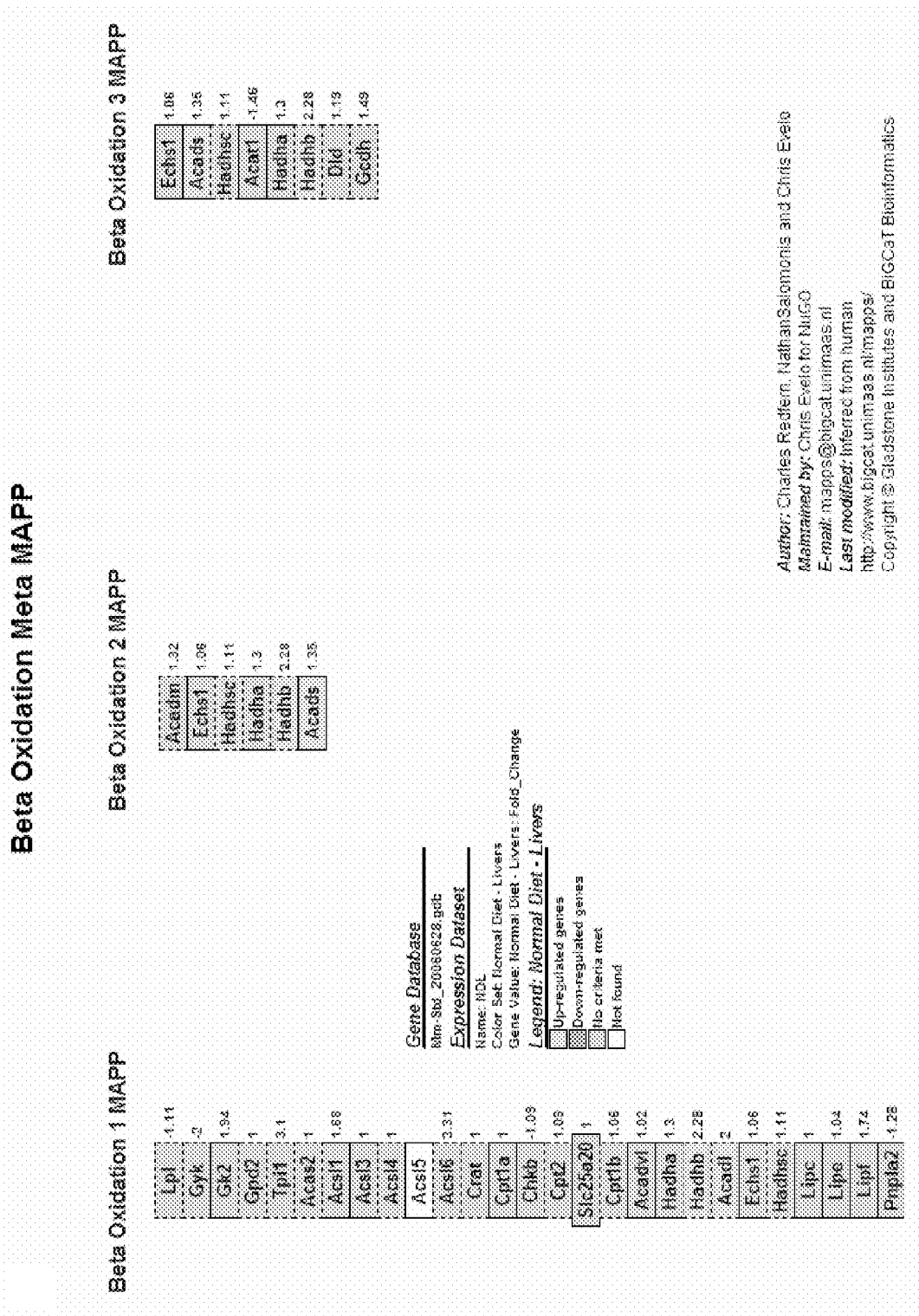
FIG. 2A depicts the GenMAPPs showing functions and genes significantly up-regulated in the liver fatty acid beta oxidation pathway by oil palm phenolics.

Oil palm phenolics up-regulated 196 genes and down-regulated 54 genes in the livers of mice on a normal diet, with the lists of genes and functions significantly changed supplemented in Additional Files 1 and 2 respectively. Functional analysis on the microarray data from the liver showed that oil palm phenolics up-regulated the fatty acid beta oxidation pathway (FIG. 2A). Among the fatty acid beta oxidation genes up-regulated were those encoding sterol carrier protein (Scp), lysophospholipase (Lypla1), mono-glyceride lipase (Mgll), acetyl-coA dehydrogenase (Acadl), acyl-coA dehydrogenases (Acads, Acad8), hydroxyacyl-coA dehydrogenases (Hadhb, Hadhsc), acetyl-coA acetyl-transferases (Acat2, Acat3) and acetyl-coA acyltransferase (Acaa2).

The liver is known as an organ active in fatty acid beta oxidation, and thus up-regulation of hepatic fatty acid beta oxidation might contribute to the suppression of liver fat and visceral fat accumulation. Up-regulated fatty acid beta oxidation may also contribute to the prevention of diabetes, which is known to be caused by obesity and insulin resistance. Up-regulation of genes involved in lipid catabolism has also been found to be caused by the catechins of green tea and the chlorogenic acid of coffee. In addition, removal of lipids from the body through fatty acid beta oxidation may prevent lipid peroxidation, which contributes to atherosclerosis. Interestingly, enhanced hepatic fatty acid synthesis and reduced fatty acid oxidation have also been implied in the development of an alcohol-induced fatty liver. Thus, we postulate that oil palm phenolics may also be able to prevent alcohol-induced liver damage by up-regulating hepatic fatty acid beta oxidation.

Figure 2B:
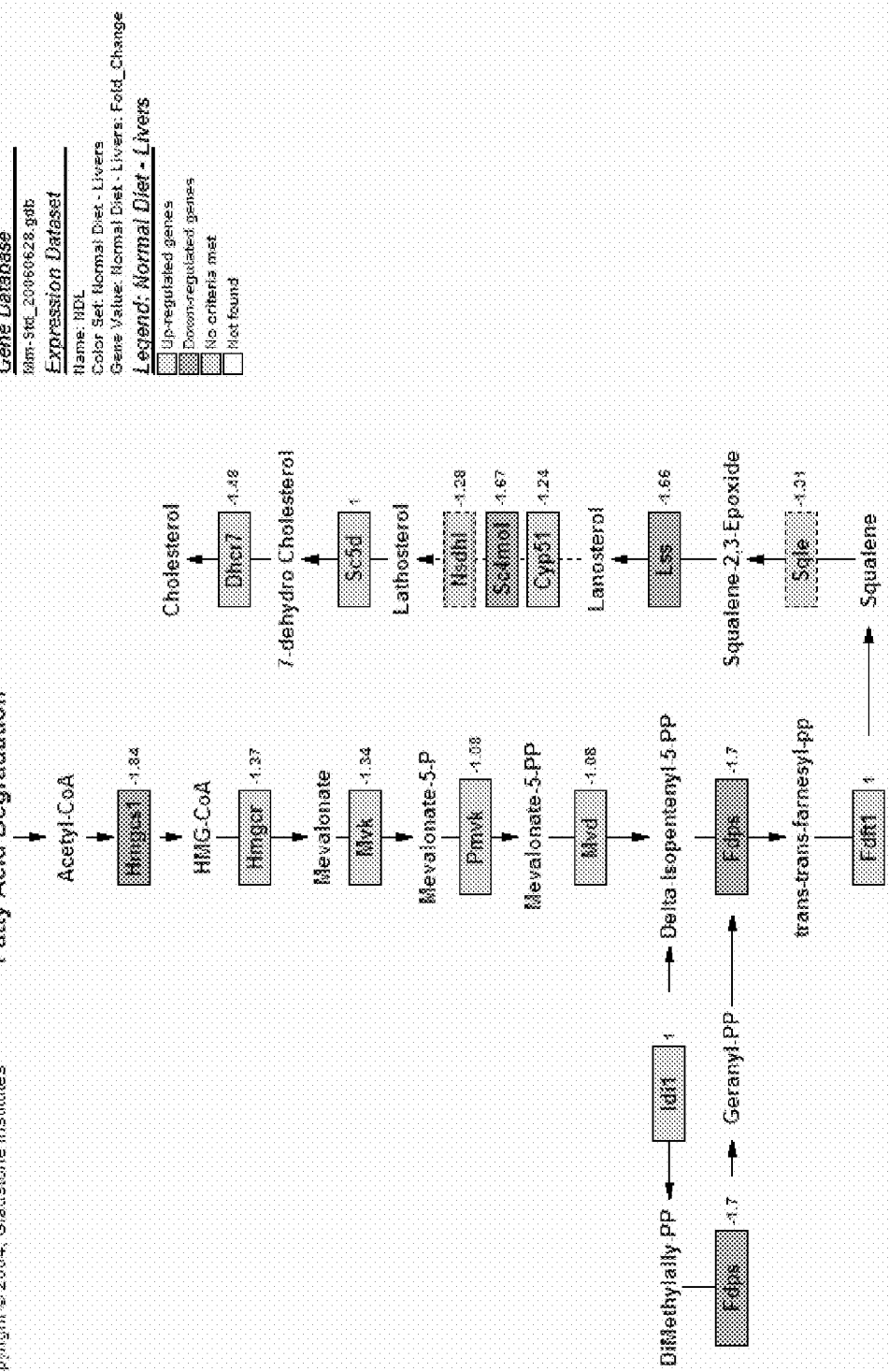
FIG. 2B depicts the GenMAPPs showing functions and genes significantly down-regulated in the liver cholesterol biosynthesis pathway by oil palm phenolics.

Genes involved in cholesterol biosynthesis on the other hand, such as those encoding lanosterol synthase (Lss), sterol-C4-methyl oxidase-like (Sc4 mol), farnesyl diphosphate synthetase (Fdps), NAD(P) dependent steroid dehydrogenase-like (Nsdhl) and 3-hydroxy-3-methylglutaryl-Coenzyme A synthase 1 (Hmgcs1) were down-regulated in this study (FIG. 2B). It should be noted that the fold changes for most of the genes in the GenMAPP were negative, indicating down-regulation, even for genes which were not selected as significantly different based on the selection criteria used. Hmgcr which encodes for 3-hydroxy-3-methylglutaryl-coenzyme-A reductase, an enzyme inhibited by cholesterol-lowering statins, showed a negative fold change as well, although the value was not significantly different.

Cholesterol is an important constituent of cellular membranes and serves as a precursor in the formation of bile acids and steroid hormones. Excessive cholesterol however, is involved in atherosclerotic lesion and gallstone formation. The results obtained suggest that cholesterol biosynthesis in the livers of these mice was reduced, and further imply that oil palm phenolics may help to prevent atherosclerosis and cardiovascular disease. These results (up-regulated fatty acid beta oxidation and down-regulated cholesterol biosynthesis in the liver) also support earlier findings that oil palm phenolics were able to improve vascular health and reduce atherosclerosis.

Gene Expression Changes in the Liver, Spleen and Heart (Atherogenic Diet Module)

The number of genes significantly changed by the atherogenic diet was highest in the liver (2593 up-regulated and 451 down-regulated), followed by the spleen (990 up-regulated and 534 down-regulated) and the heart (1441 up-regulated and 991 down-regulated). The number of genes significantly changed by oil palm phenolics was highest in the spleen (327 up-regulated and 249 down-regulated), followed by the liver (35 up-regulated and 84 down-regulated) and the heart (19 up-regulated and 13 down-regulated). In the latter comparison, as the heart showed the least number of genes significantly changed (32 genes) which would not give much information in further functional analysis, we further reduced this stringency by filtering for significantly changed genes with a |Differential Score| of more than 13, which was equivalent to a P Value of less than 0.05. This yielded 132 significantly changed genes in the heart (79 up-regulated and 53 down-regulated). The lists of genes significantly changed by the atherogenic diet and oil palm phenolics in these mouse organs, together with the fold changes, are supplemented in Additional Files 3 and 4 respectively. The lists of GenMAPPSs and gene ontologies significantly changed by the atherogenic diet and oil palm phenolics in the major organs analyzed are given in Additional Files 5 and 6 respectively.

Figure 3A:
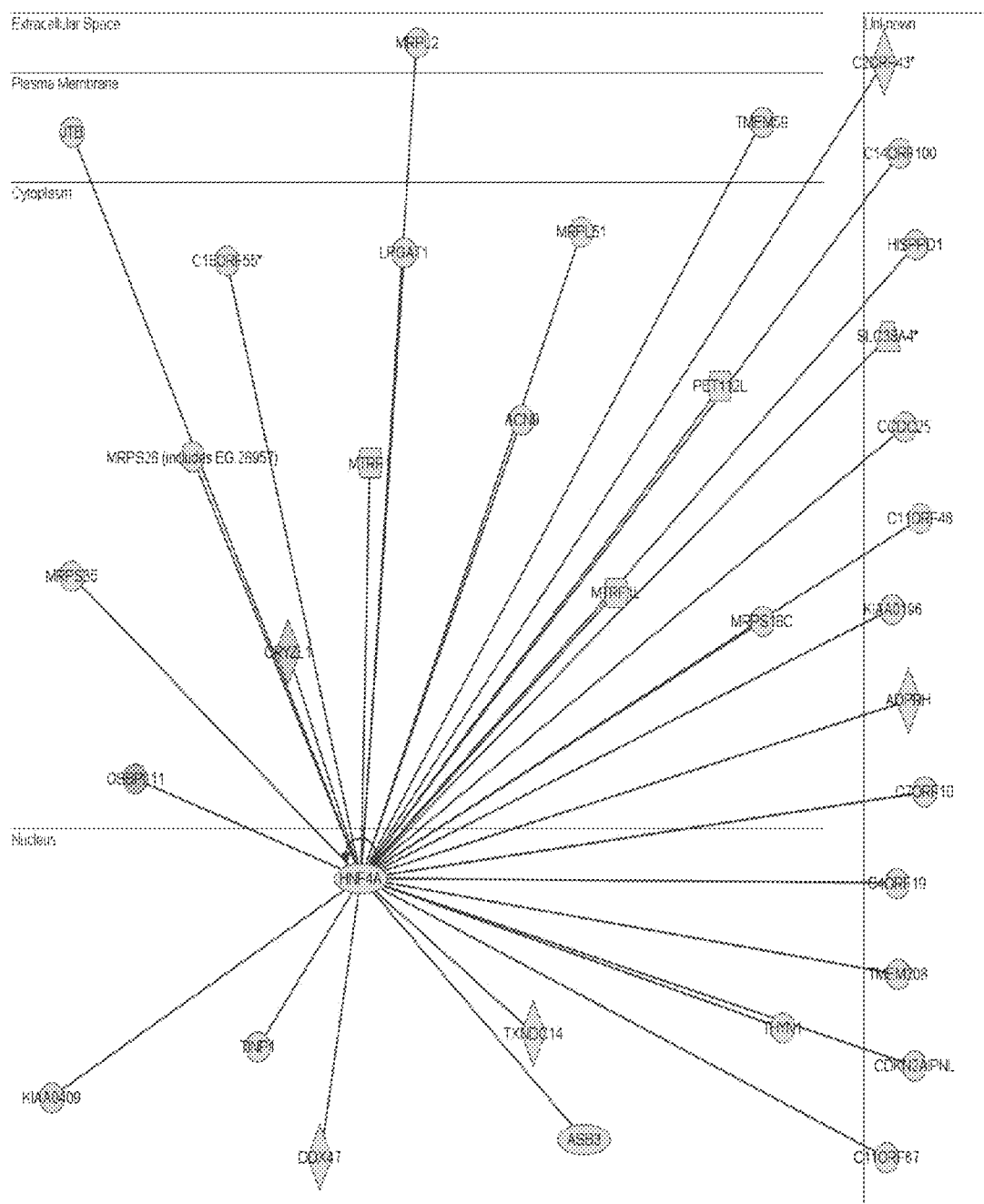
FIG. 3A shows that the genes up-regulated by the Atherogenic Diet in the liver are linked to Hnf4a, which is a nuclear factor involved in hepatocyte differentiation.
Figure 3B:
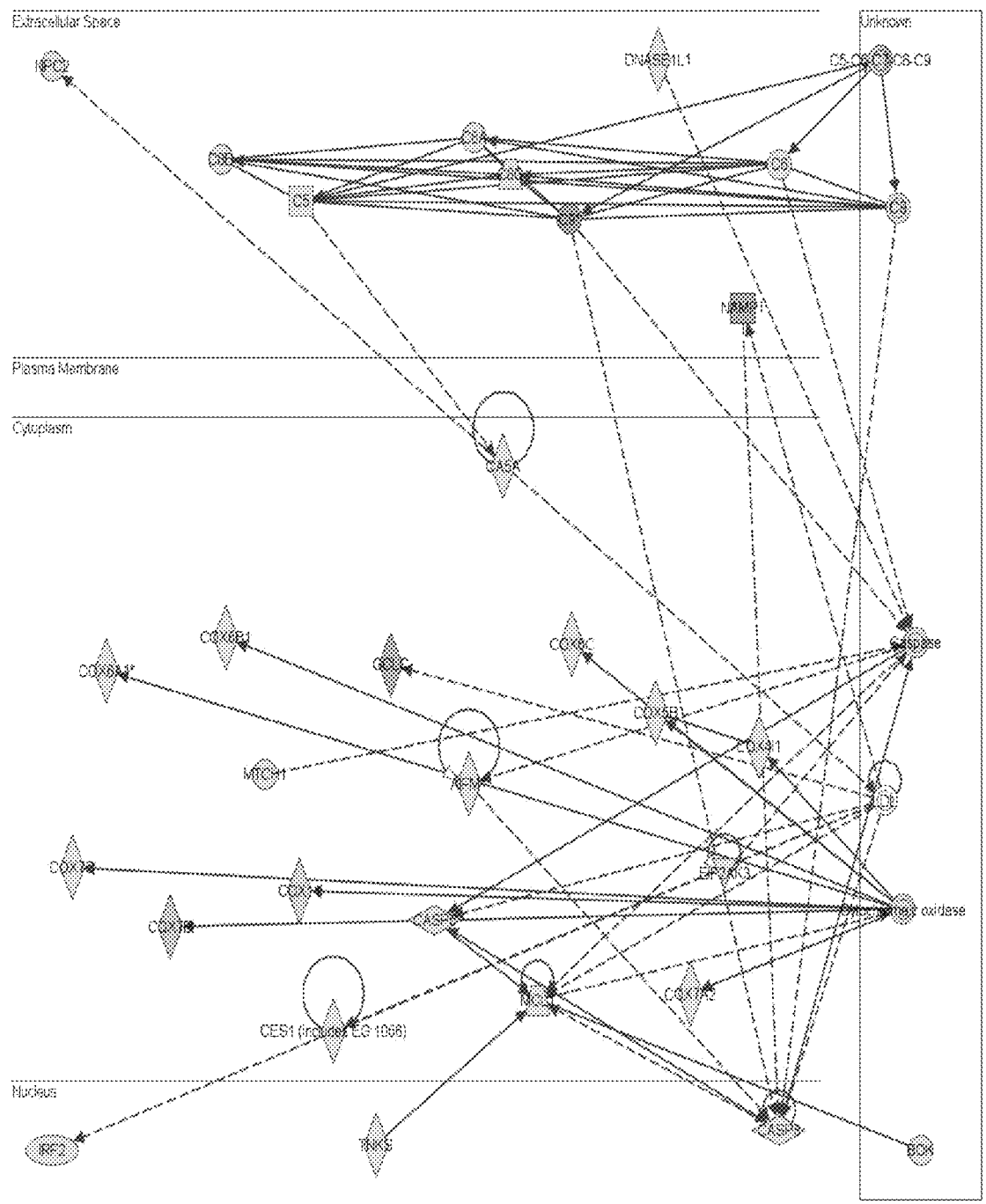
FIG. 3B shows that the up-regulated genes include cytochrome c oxidases, caspases and complement genes, which are involved in cell death via apoptosis.

Increased Intake of Dietary Fat and Cholesterol Up-Regulated Liver Regeneration and Down-Regulated Hepatic Cholesterol Biosynthesis Administration of the atherogenic diet increased the turnover of metabolites in the liver, as shown by an up-regulation of genes involved in the generation of precursor metabolites (anabolism) and energy (catabolism). It was also evident that genes involved in fatty acid beta oxidation, the tricarboxylic acid cycle and the electron transport chain were up-regulated, thus suggesting an increase in energy production due to the utilization of extra fat. In addition, the turnover of liver tissues was also evident, due to the up-regulation of nuclear receptors which stimulate hepatocyte growth such as Hnf4a (FIG. 3A) as well as cytochrome c oxidases, complement genes and caspases involved in cell death (FIG. 3B).

Up-regulation of the fatty acid beta oxidation process would increase the metabolism of extra fatty acids obtained from the atherogenic diet. This eventually results in an increased energy production through the tricarboxylic acid cycle and electron transport chain. When challenged with the atherogenic diet, the liver thus adjusts its metabolic processes in relation to lipid metabolism and energy production. Interestingly, mitochondrial metabolism has been implicated in the production of free radicals and degenerative diseases. It is thus possible that the increase in energy production caused an increase in the production of free radicals in the liver as well, thus resulting in oxidative stress.

As a result of this oxidative insult, nuclear receptors involved in tissue growth and genes involved in cell death were up-regulated, thus suggesting that the atherogenic diet triggered hepatic inflammatory reprogramming and liver regeneration in the mice. This also explains the enlargement of livers which was observed in these animals. An example of a nuclear receptor up-regulated is the hepatocyte nuclear factor 4-alpha (Hnf4a), which was also found to be up-regulated when ApoE3Leiden (E3L) mice (which have lipid profiles resembling those of humans) were fed an atherogenic diet. Hnf4a is central to the maintenance of hepatocyte differentiation and is a major in vivo regulator of genes involved in the control of lipid homeostasis. The up-regulation of this gene and other genes associated with it suggests the important role of Hnf4a in maintaining the proper function of the liver when challenged by oxidative stress.

Among the genes involved in cell death include those encoding cytochrome c oxidases belonging to the mitochondrial electron transport chain, complement genes and caspases. The up-regulation of these genes suggests that cell death occurred via apoptosis as a result of complement-mediated cell damage. Activation of the terminal pathway of the complement system leads to insertion of terminal complement complexes (C5b-9) into the cell membrane, which may induce cytolysis. Recent data also indicate that the terminal complement pathway (C5b-9) is involved in the induction of apoptosis via a caspase-dependent pathway. Incidentally, besides being involved in the electron transport chain, cytochrome c oxidases are essential in the apoptotic process. The up-regulation of these three groups of genes in the same network thus implies that the atherogenic diet caused complement activation, resulting in cell death via apoptosis. Interestingly, induction of the complement pathway in the liver has also been associated with lesion development in atherosclerosis-prone LDL receptor-deficient ($LDLr^{-/-}$) mice when they were fed a high-fat Western-style diet.

Figure 4:
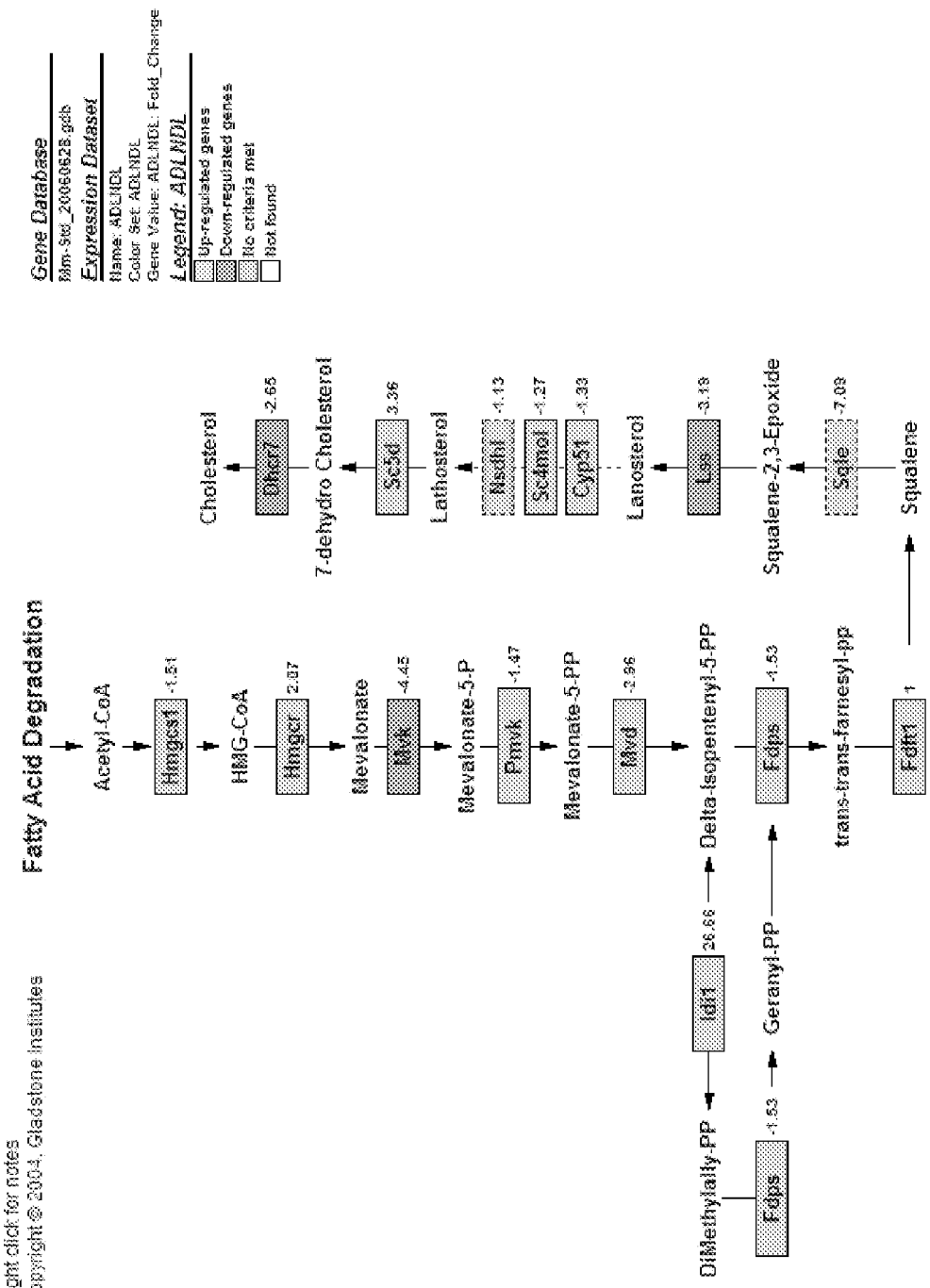
FIG. 4 is a diagram of genes down-regulated by the Atherogenic Diet in the Liver Cholesterol Biosynthesis Pathway.

As expected, genes involved in cholesterol biosynthesis were down-regulated by the atherogenic diet (FIG. 4). Plasma or serum cholesterol levels are determined by inputs from both diets and de novo biosynthesis, utilization of cholesterol especially in the liver and steroidogenic tissues, as well as excretion of either cholesterol or bile acids. As the atherogenic diet provided dietary cholesterol which further increased cholesterol levels in the blood circulation, genes involved in hepatic cholesterol biosynthesis were down-regulated in this study. This observation is expected due to the fact that de novo cholesterol biosynthesis is down-regulated when cholesterol is available from dietary intake, and partly validates the microarray gene expression data obtained.

A Heightened Production and Turnover of Immune Cells was Caused by the Atherogenic Diet in the Spleen The immune system has long been implicated in atherosclerosis, which is caused by an inflammatory response. This response is mediated by endothelial cells, platelets, monocyte-derived macrophages, dendritic cells, mast cells and specific subtypes of T lymphocytes or T cells. Advanced human atheromas also contain a heterogeneous population of T cell receptors. Some dendritic cells cluster with T cells directly within atherosclerotic lesions, while others migrate to lymphoid organs to activate T cells. Macrophages, endothelial cells and smooth muscle cells appear to be activated based on their expression of MHC class II molecules and numerous inflammatory products. In addition, bone-marrow cells including hematopoietic stem cells, also contribute to the pathological remodelling in atherosclerosis by differentiating into smooth muscle cells. Non-bone marrow-derived circulating progenitor cells in the adventitia of atherosclerotic lesions might also be a source for smooth muscle cells, macrophages and endothelial cells in these lesions, besides the migration of these cells from the tunica media.

Figure 5A:
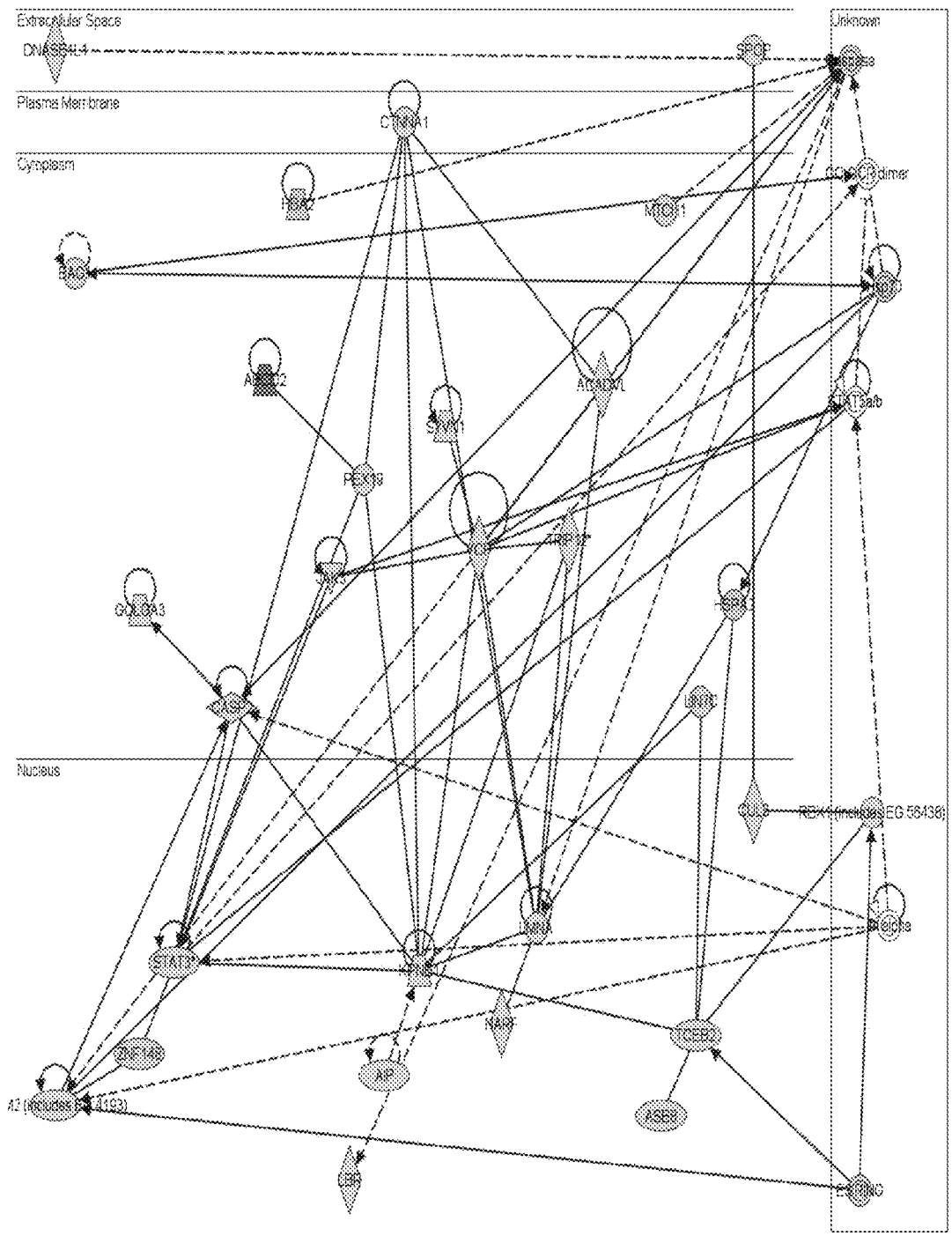
FIG. 5A is a diagram of genes up-regulated by the Atherogenic Diet in the Stat3 network (e.g., in the Spleen)
Figure 5B:
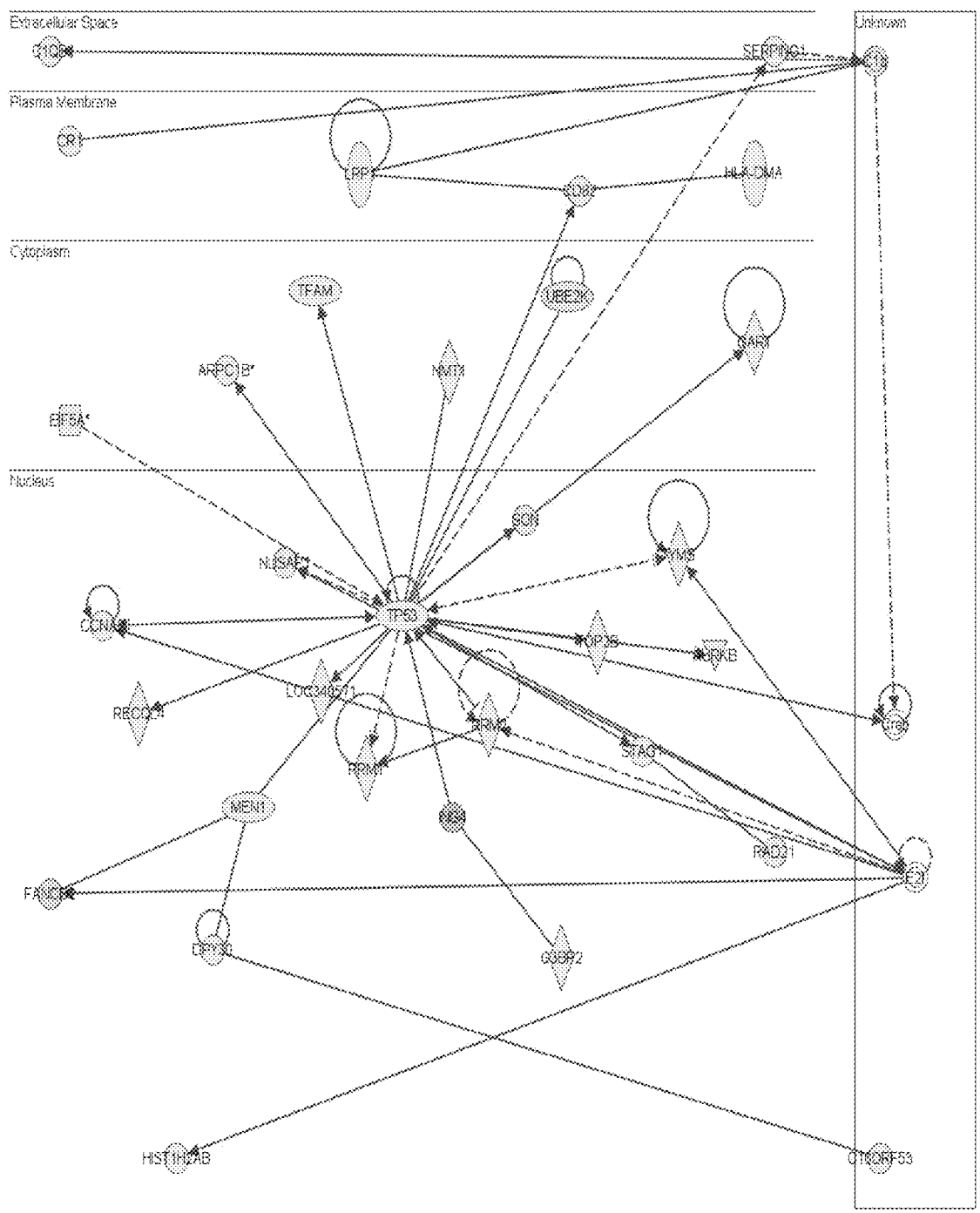
FIG. 5B is a diagram of genes down-regulated in the Tp53 network.

In this study, genes involved in the immune response were up-regulated by the atherogenic diet in the spleen, such as those regulated by tumour necrosis factor-alpha (Tnfa) and signal transducer and activator of transcription 3 (Stat3) (FIG. 5A). In addition, the apoptotic process was also found to be up-regulated. On the other hand, genes down-regulated by the atherogenic diet include those regulated by the tumour suppressor Tp53 (FIG. 5B) and transforming growth factor-beta (Tgfb1). Tp53 is anti-proliferative while Tgfb1 is anti-inflammatory. The up-regulation of Tnfa and Stat3, coupled with the down-regulation of Tp53 and Tgfb1, suggests the up-regulation of an inflammatory response towards the atherogenic diet.

It is interesting to note that Stat3 was discovered because of its role in the acute phase response, and that this is the only capacity in which its function in vivo can be clearly ascribed to its activity as a transcription factor. Stat3 is important for hematopoietic homeostasis as it plays a critical role in mediating cellular responses involved in the production of immature and committed hematopoietic progenitors. In addition, Stat3 has been implicated in many human lymphoproliferative and myeloproliferative diseases, including multiple myeloma, non-Hodgkin lymphoma and acute myeloid leukemia, that display deregulated Stat3 activation. In support of the observation that the Stat3 network was up-regulated, the B cell receptor pathway was also up-regulated in this study, further advocating the role of Stat3 in encouraging the proliferation of immune cells. Together with the up-regulation of the Stat3 network, B cell receptor pathway and apoptosis, the down-regulation of the tumour suppressor Tp53 implies that the atherogenic diet caused an increased turnover of immune cells in the spleen, and thus explains the increased production and deployment of immune cells in the blood circulation, which may further excerbate the in vivo inflammatory effects of the atherogenic diet in this study.

The Atherogenic Diet Triggered an Inflammatory Response in the Heart

Figure 6A:
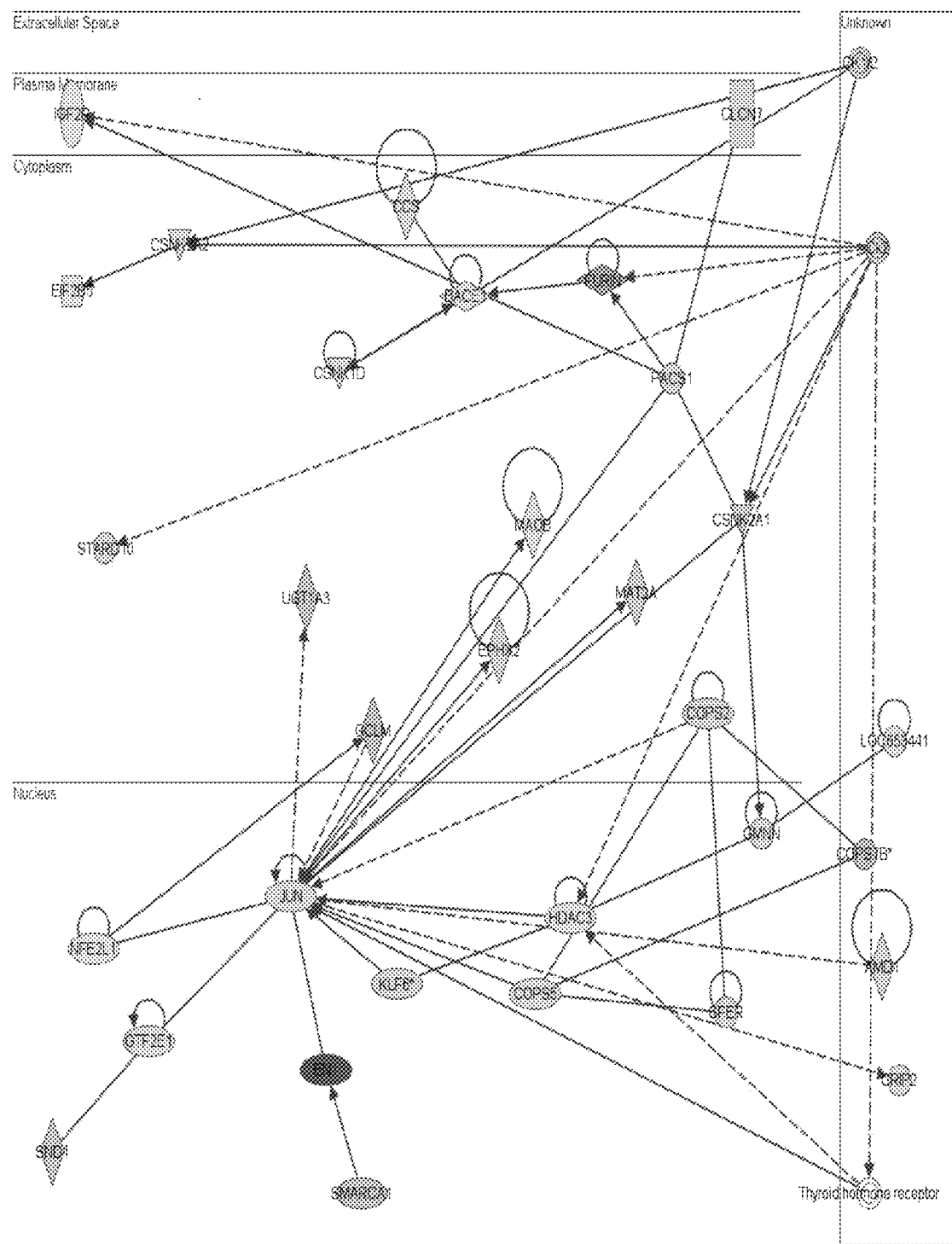
FIG. 6A is a diagram of genes up-regulated by the Atherogenic Diet in the Jun network (e.g., in the heart)
Figure 6B:
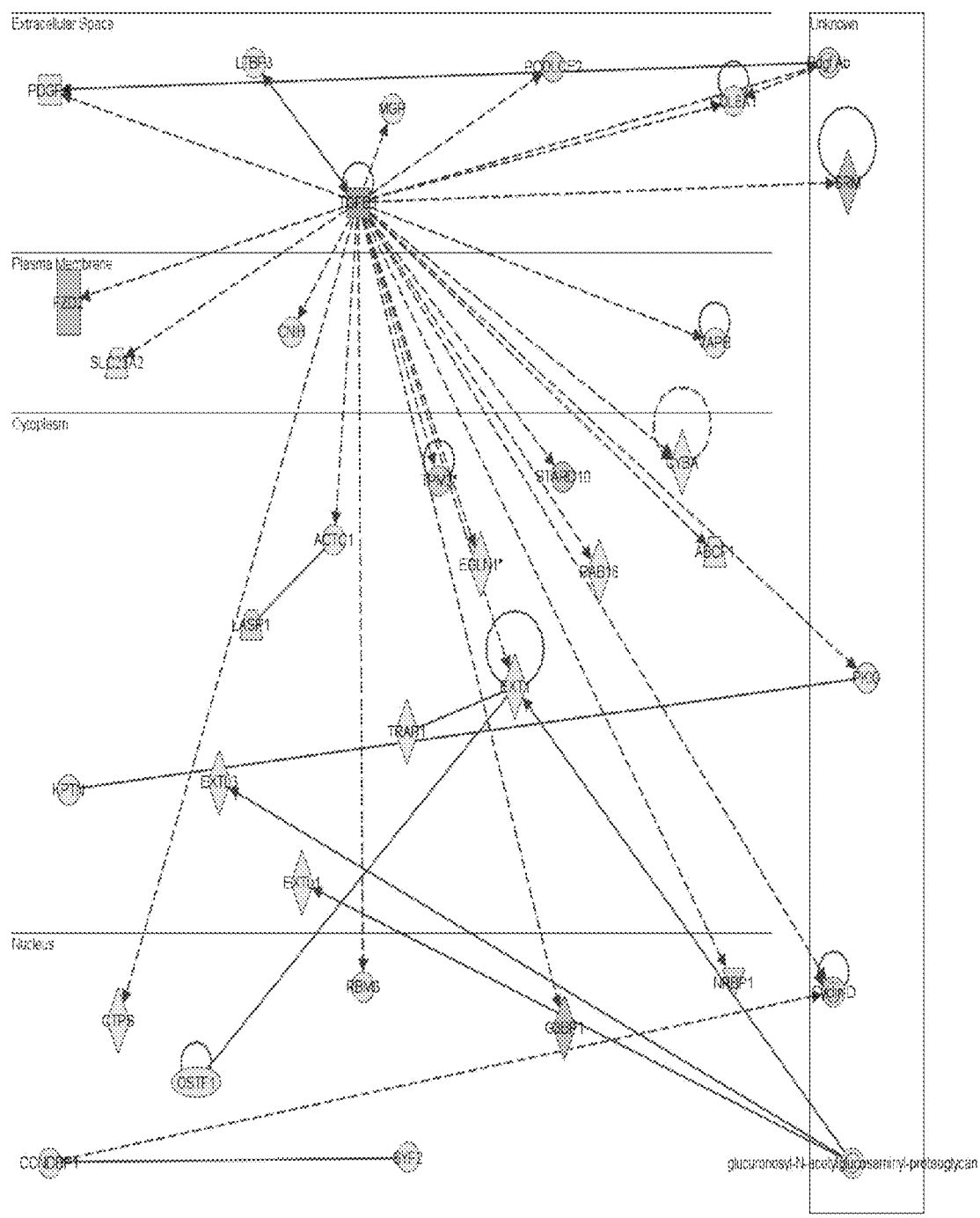
FIG. 6B is a diagram of genes down-regulated in the Tgfb1 network.

In the heart, the atherogenic diet increased the expression of genes involved in fatty acid beta oxidation, proteasomal degradation, heme biosynthesis as well as inflammation including those regulated by Tnfa, CREB (cyclic adenosine monophosphate response element binding) binding protein (Crebbp) and Jun oncogene which is part of activator protein-1 (Ap-1) (FIG. 6A). Down-regulated genes were found to be involved in glycolysis, circadian rhythm, muscle development and anti-inflammatory networks such as those regulated by sirtuin 1 (Sin1) and Tgfb1 (FIG. 6B).

The Jun protein forms part of the transcription factor AP-1, which is pro-inflammatory as it has been implicated in oxidative stress. Binding sites of the redox-regulated transcription factor AP-1 are located in the promoter region of a large variety of genes that are directly involved in the pathogenesis of diseases, including atherosclerosis. Activation of Jun via Jun amino-terminal kinase (Jnk) in response to various forms of stress causes arterial injury and heart disease. In addition, heme biosynthesis was also up-regulated by the atherogenic diet in the heart, and this suggests increased turnover of red blood cells, most probably caused by oxidative stress brought about by the diet.

On the other hand, Tgfb has been suggested to be anti-inflammatory in atherosclerosis, as it plays an important role in the maintenance of normal blood vessel structure, while defects in this superfamily of genes have been linked to a range of cardiovascular syndromes including loss of healthy vessel architecture and aneurysm. Microarray profiling carried out on the aortas from apolipoprotein E-deficient (apoE$^{-/-}$) mice on a high-fat diet compared with control C57Bl/6J and C3H mice across time also showed a decreased expression of an isoform of Tgfb. The down-regulation of the Tgfb1 gene in this study thus implies a pro-inflammatory response to the atherogenic diet in the heart.

Figure 7:
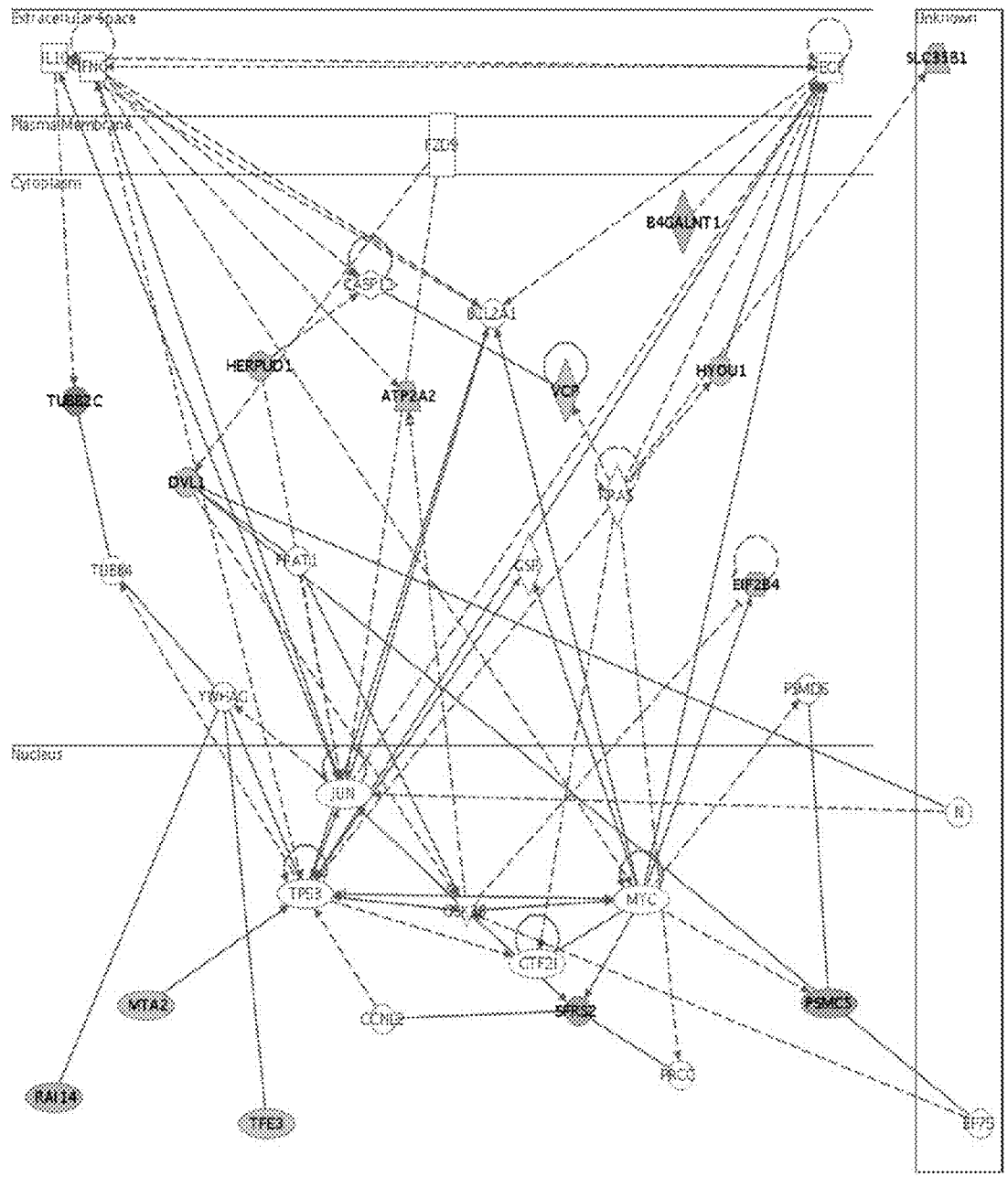
FIG. 7 is a diagram of genes up-regulated by oil palm phenolics in the liver unfolded protein response network.

The Unfolded Protein Response was Up-Regulated by Oil Palm Phenolics in the Liver In livers of mice belonging to the atherogenic diet treatment group, genes involved in the unfolded protein response were up-regulated (FIG. 7) by oil palm phenolics compared to the atherogenic diet control group. Down-regulation of genes involved in endogenous antigen presentation, fatty acid metabolism, arylsulfatase activity, NADH dehydrogenase (ubiquinone) activity and oxidoreductase activity were also observed, indicating a down-regulation of the inflammatory response and energy production.

Up-regulated genes involved in the unfolded protein response include Herpud1, Tra1 and Vcp. Unfolded protein response can be promoted by the buildup of unfolded proteins in the endoplasmic reticulum and constitutes a mechanism to reduce this burden. It acutely reduces translation of new proteins, followed by increased expression of chaperones to aid folding of existing proteins and enhanced elimination of proteins that cannot be refolded. Endoplasmic reticulum stress responsive genes have been suggested to be a protective response to protein unfolding or protein damage resulting from cellular stress signals. Accordingly, decreased expression of Herpud1 were reported to be found in prostate cancer patient specimens. Thus, oil palm phenolics may help to reduce the amount of damaged proteins caused by the atherogenic diet in the liver and thus lessen its turnover and metabolic burden.

Another interesting gene found regulated was Keap1, which was down-regulated by the atherogenic diet but up-regulated by oil palm phenolics. Keap1 is an inhibitor of Nrf2, which normally sequesters Nrf2 in the cytoplasm. Under oxidative stress, the cysteine residues of Keap1 are oxidized and Nrf2 migrates to the nucleus to activate phase II antioxidant enzymes. Of particular interest, KIAA0132, a human homolog of Keap1, was up-regulated by tert-butylhydroquinone (tBHQ), a strong inducer of phase II detoxification enzymes via activation of the antioxidant responsive element (ARE). Putative Nrf2 binding sites in the 5'-flanking region of KIAA0132 also indicate that transcription of KIAA0132 can be increased by the transcription factor that it sequesters, and thus this feedback effect may aim to keep in balance the expression of ARE-driven genes.

Down-regulation of genes involved in endogenous antigen presentation such as H2-T23, H2-T10, Cd59a and Mug1 may be a mechanism by which oil palm phenolics reduce inflammation brought about by the atherogenic diet. Genes involved in fatty acid metabolism were also down-regulated, including Cpt2, Pecr, Acas2, Fads2, Abcd3 and Abcg2. Fads2 encodes the rate-limiting enzyme in the synthesis of long-chain polyunsaturated fatty acids. This function includes the synthesis of arachidonic acid that is needed for synthesis of the eicosanoid biomediators that play central roles in cell signalling, cardiovascular regulation, inflammation and blood coagulation.

Down-Regulation of Antigen Presentation in the Spleen Implies that Oil Palm Phenolics Attenuated the Inflammatory Response Compared to the atherogenic diet control group, genes up-regulated in spleens of mice in the atherogenic diet treatment group are those involved in carbohydrate metabolism, glucose metabolism, glutathione metabolism as well as cytoskeleton organization and biogenesis. Genes down-regulated by oil palm phenolics in spleens of mice are involved in antigen presentation (FIG. 8), apoptosis, B cell receptor signalling, defence response, genes specific to blood and lymph tissues, heme biosynthesis, immune response, regulation of apoptosis, T cell activation and differentiation as well as T cell receptor signalling.

Transketolase (Tkt), which controls the nonoxidative branch of the pentose phosphate pathway, provides NADPH for biosynthesis and reducing power for several antioxidant systems [82]. It was up-regulated in the spleen by oil palm phenolics, together with glucose-6-phosphate dehydrogenase (X-linked) (G6pdx) and phosphogluconate dehydrogenase (Pgd), all of which are involved in the pentose phosphate pathway. The products of the pentose phosphate pathway are important for the biosynthesis of purine and for stimulating antioxidant response pathways in conjunction with the action of dietary phenolic antioxidants. This may also explain the up-regulation of antioxidant genes including Mgst1, Mgst2, Gsr and Gstm1 in the spleen by oil palm phenolics. Additionally, genes encoding stefins (Stfa1, Stfa2) were up-regulated as well. These cystatins are natural inhibitors of cysteine cathepsins, which have been implicated in antigen presentation and inflammation. In addition, Anxa2, a phospholipase inhibitor, was up-regulated.

Annexin A2 is a pleiotropic protein which has been proposed to function inside the cell in sorting of endosomes and outside the cell in anti-coagulant reactions.

Genes encoding MHC molecules such as H2-Ab1 and H2-Eb1 which have been implicated in atherosclerosis, were down-regulated in the spleen, thus suggesting that oil palm phenolics were able to attenuate the inflammatory response brought about by the atherogenic diet. Other MHC genes down-regulated include H2-Aa, H2-Bf, H2-Dma, H2-DMb2, H2-Ea, H2-Q6, H2-Q7, H2-T9, H2-T10, H2-T17 and H2-T23. Activated macrophages and smooth muscle cells express MHC II antigens such as HLA-DR that allow them to present antigens to T cells, which cause atherosclerosis. In addition, MHC II expression is also central to the immune regulation in T cell-mediated autoimmune diseases.

Figure 8:
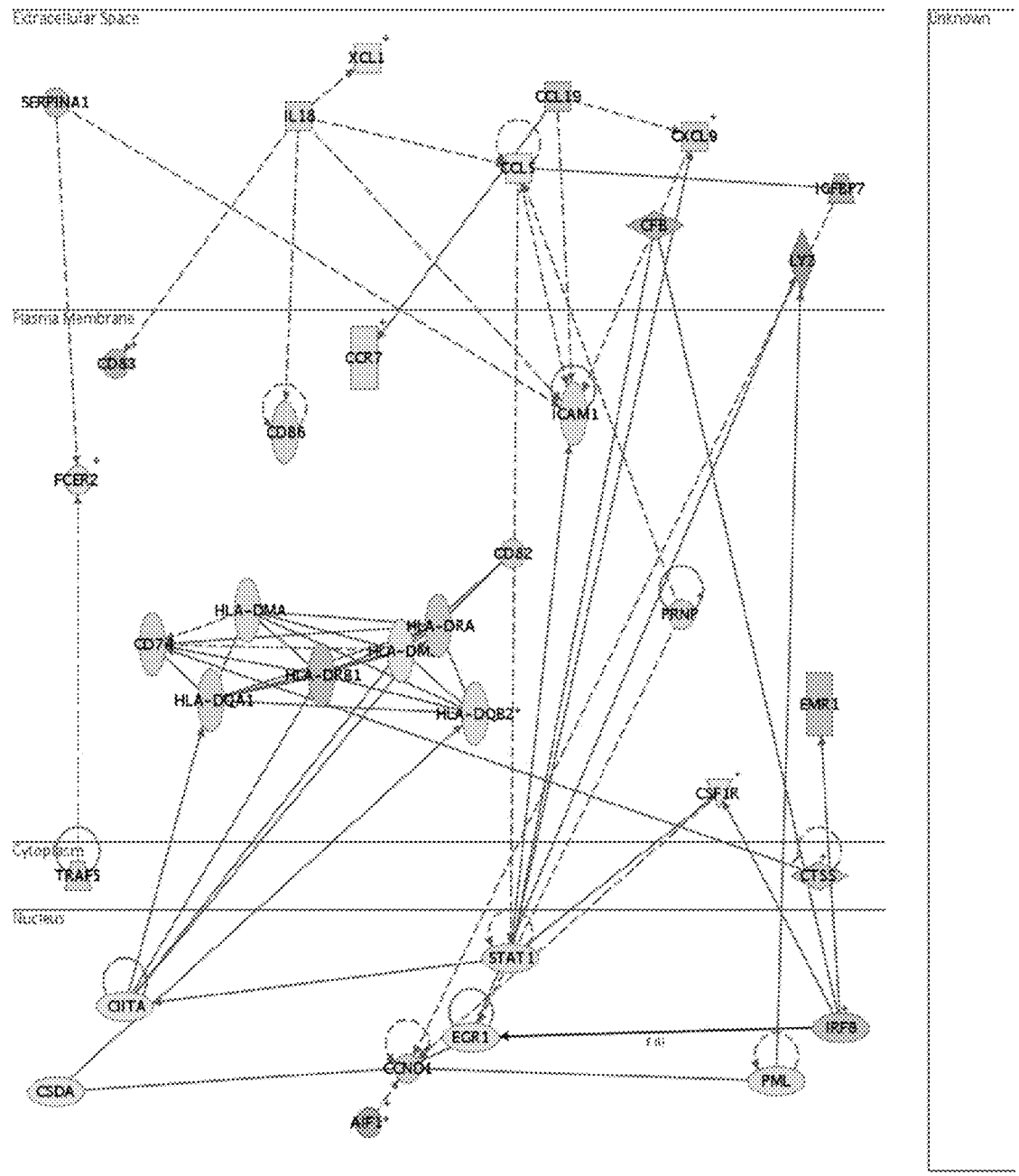
FIG. 8 is a diagram of genes down-regulated by oil palm phenolics in the spleen antigen presentation network.

The gene expression of MHC II molecules are transcriptionally regulated by the class II transcriptional activator (CIITA or C2ta). CIITA activates the expression of MHC II in all types of professional antigen-presenting cells (macrophages, dendritic cells, B lymphocytes), of which dendritic cells are the most potent among the three. Interferon-γ represses collagen synthesis and increases the expression of MHC II molecules in aortic smooth muscle cells through CIITA, contributing to atherosclerosis. In line with the down-regulation of major histocompatibility complexes, the C2ta gene was down-regulated in this study (FIG. 8). This is similar to the effects of statins, which are largely used in the treatment of cardiovascular disease not only because of their therapeutic effect in lowering cholesterol levels but also in decreasing the expression of MHC II genes, in which C2ta has been demonstrated as a target.

The Ccr7 receptor present on the surface of secondary lymphoid cells, functions to attract dendritic cells which migrate to secondary lymphoid organs to present antigens to activate naive T cells. A mechanism of anti-inflammation by antioxidants is through the modulation of cytokine induction during inflammation. In line with this, cytokines and cytokine receptors such as Ccl5, Ccl19 and Ccr7 were down-regulated by oil palm phenolics in this study. Additionally, antigenic markers such as Cd3d, Cd24a, Cd59b, Cd72, Cd79a, Cd79b, Cd83 and Cd86 were down-regulated. These markers are present on dendritic cells and interact with counter-receptors on T cells to enhance co-stimulation and adhesion. Cd83 and Cd86 are specific markers of mature dendritic cells, which are up-regulated by oxidative stress through a NF-κB-dependent mechanism. The down-regulation of MHC II genes and genes encoding antigenic markers thus suggests that oil palm phenolics suppressed the inflammatory response associated with the atherogenic diet, and this may represent a mechanism by which oil palm phenolics ameliorate atherosclerosis.

Antioxidant Genes were Up-Regulated by Oil Palm Phenolics in the Heart

Figure 9:
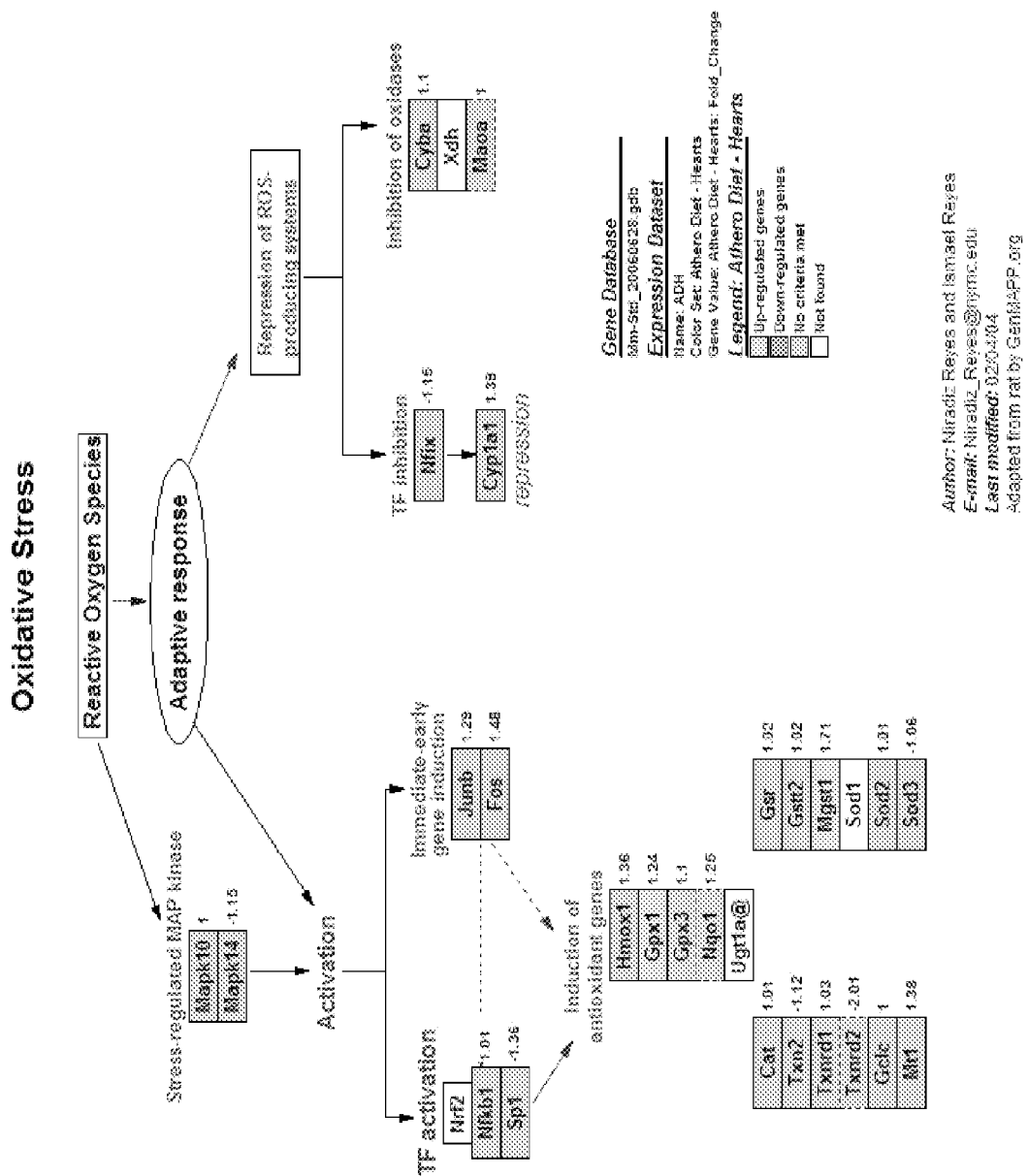
FIG. 9 is a diagram of genes up-regulated by oil palm phenolics in the heart antioxidant pathway.

In hearts of mice, genes up-regulated by oil palm phenolics include those involved in oxidative stress (FIG. 9), circadian exercise and nucleosome assembly. Down-regulated genes on the other hand, are involved in electron transport and signalling as well as cell proliferation and migration.

Up-regulated genes involved in antioxidant activities include Mgst1 and Gpx1. These antioxidant genes are essential in the detoxification of carcinogens and scavenging of reactive oxygen species. Fstl1 or TSC-36, which has been shown to inhibit the proliferation of vascular smooth muscle cells in vitro and in vivo following stimulation of TGF-β, was up-regulated as well. Down-regulated genes on the other hand, are involved in electron transport and signalling. Genes involved in cell proliferation and migration (which have been implicated in atherosclerosis), such as Egf, Ltbp4, Smtn, Vtn and Lgals4 were down-regulated as well. Alas2, a gene which is red cell specific, was also down-regulated. This is in contrast with the observation that the atherogenic diet up-regulated genes involved in heme biosynthesis, which further indicates that oil palm phenolics decreased heme turnover caused by the atherogenic diet and thus functioned to reduce oxidative stress in the heart.

Figure 10:
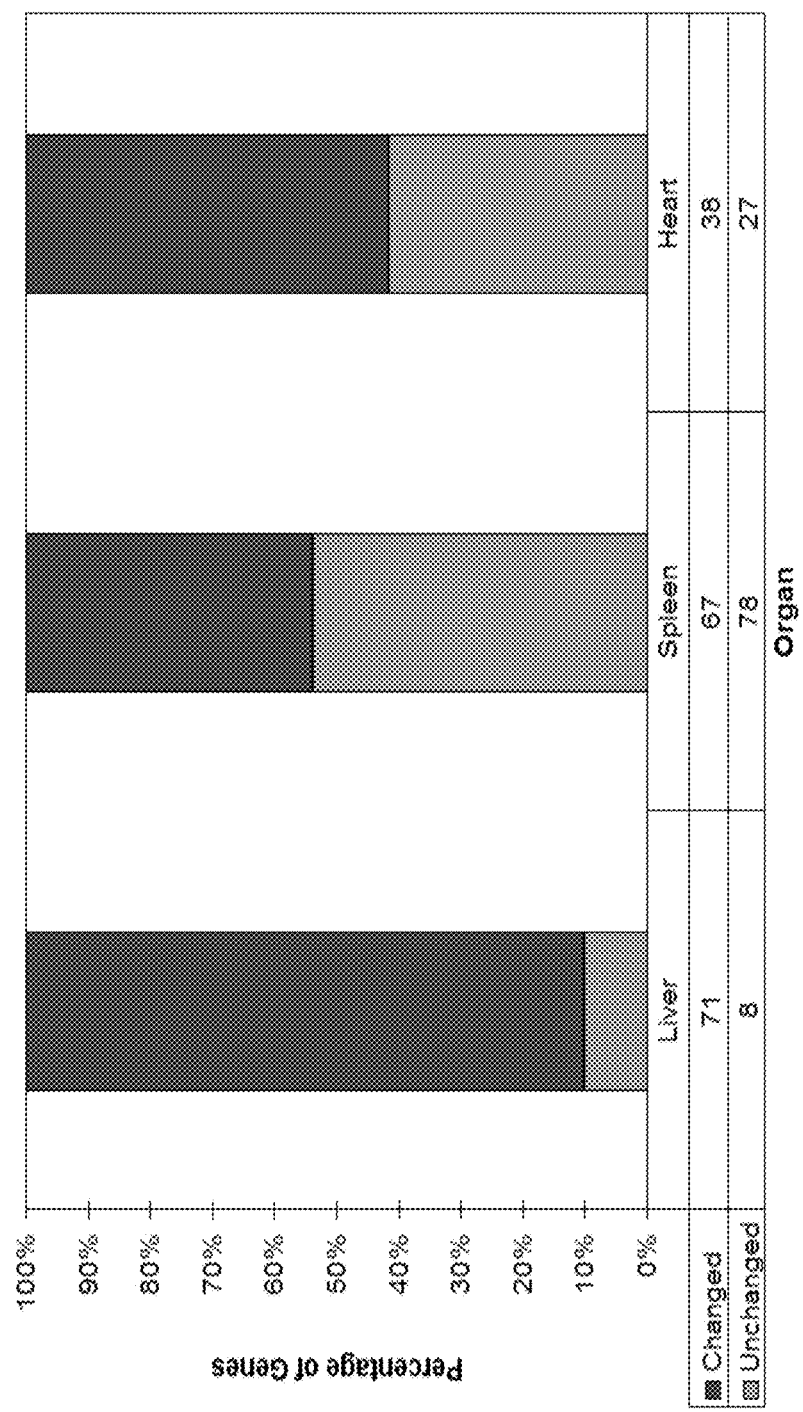
FIG. 10 is a diagram of the percentage of genes which showed a change in direction when regulated by oil palm phenolics as compared to the atherogenic diet.
Figure 11A:
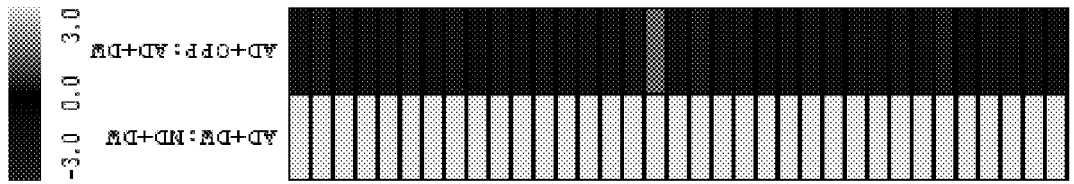
FIGS. 11A and 11B show a comparison of genes that are significantly changed by the atherogenic diet and oil palm phenolics in terms of the direction of fold changes (liver data as example)
Figure 11B:
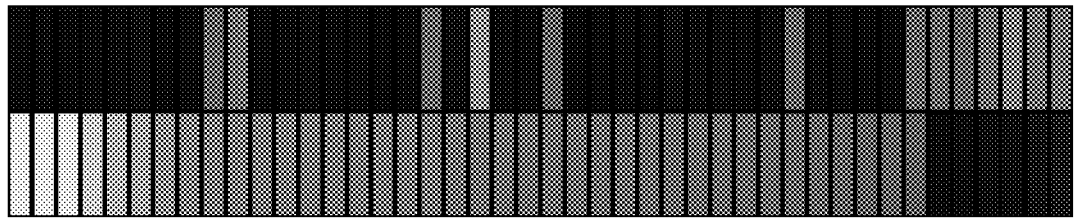

Comparison of Genes Significantly Changed by the Atherogenic Diet and Oil Palm Phenolics In order to assess how oil palm phenolics affected genes changed by the atherogenic diet, genes significantly changed by the atherogenic diet were intersected with genes significantly changed by oil palm phenolics in the atherogenic diet module to obtain a set of genes which were significantly regulated by both factors (atherogenic diet and oil palm phenolics). This comparison is given in Additional File 7. The percentages of genes which were differentially regulated by both factors in terms of direction were then calculated, with the results shown in FIG. 10. A majority (>50%) of the genes regulated by oil palm phenolics in the different organs showed a difference in direction of regulation when compared to the atherogenic diet. The highest percentage of change was found in the liver while the lowest percentage of change was found in the spleen. FIGS. 11A and 11B together provide a diagram which compares the fold change direction of genes significantly changed by the atherogenic diet and oil palm phenolics, using the liver as an example.

Unchanged changes are genes which show a similar direction of regulation by the atherogenic diet and oil palm phenolics while changed genes showed an opposite direction of regulation by the two factors. The percentage of changed genes was calculated by dividing the amount of genes which changed in terms of direction of regulation with the total number of genes significantly changed by both factors.

ND+DW indicates Normal Diet+Distilled Water, AD+DW indicates Atherogenic Diet+Distilled Water and AD+OPP indicates Atherogenic Diet+Oil Palm Phenolics. Values of fold changes are represented using a blue-black-yellow (negative to positive) colour scheme. The |Differential Score| for all genes is more than 20, equivalent to a P Value of less than 0.01.

Real-Time qRT-PCR Validation

To confirm the microarray results, the expression levels of eight target genes (Table 3) were measured using real-time quantitative reverse transcription-polymerase chain reaction (qRT-PCR). The first two target genes were found to be changed by oil palm phenolics in the normal diet module (first comparison). For the atherogenic diet module, as the focus of this study was more to identifying the changes caused by oil palm phenolics rather than the atherogenic diet, the remaining six target genes chosen for real-time qRT-PCR were from the third comparison (Atherogenic Diet+Oil Palm Phenolics: Atherogenic Diet+Distilled Water). The genes were chosen based on their differential scores, in which the most significantly up-regulated and down-regulated genes in each of the organ tested were selected.

TABLE 3

Genes Selected for the Real-Time qRT-PCR Validation Experiments

| Organ | Symbol | Definition | Accession | Assay ID |
|---|---|---|---|---|
| Liver | Cyp3a11 | *Mus musculus* cytochrome P450, family 3, subfamily a, polypeptide 11 | NM_007818 | Mm00731567_m1 |
| Liver | Hmgcs1 | *Mus musculus* 3-hydroxy-3-methyl-glutaryl-Coenzyme A synthase 1 | NM_145942 | Mm00524111_m1 |
| Liver | Herpud1 | *Mus musculus* ubiquitin-like domain member 1 | NM_022331 | Mm00445600_m1 |
| Liver | Fads2 | *Mus musculus* fatty acid desaturase 2 | NM_019699 | Mm00517221_m1 |
| Spleen | Anxa2 | *Mus musculus* annexin A2 | NM_007585 | Mm00500307_m1 |
| Spleen | Cfb | *Mus musculus* histocompatibility 2, complement component factor B | NM_008198 | Mm00433909_m1 |
| Heart | Fstl1 | *Mus musculus* follistatin-like 1 | NM_008047 | Mm00433371_m1 |
| Heart | Alas2 | *Mus musculus* aminolevulinic acid synthase 2, erythroid | NM_009653 | Mm00802083_m1 |
| All | Sfrs9* | *Mus musculus* splicing factor, arginine/serine rich 9 | NM_025573 | Mm00470546_m1 |
| All | Guk1* | *Mus musculus* guanylate kinase 1 | NM_008193 | Mm00433888_m1 |
| All | Hnrpab* | *Mus musculus* heterogeneous nuclear ribonucleoprotein A/B | NM_010448 | Mm00468938_m1 |

*Housekeeping gene.

These genes were also present in the GenMAPPs and gene ontologies identified as significantly changed by the GenMAPP software. These genes also showed detection levels of 1.0000 in both the control and treatment groups, which indicate that they were significantly expressed in both groups. In addition, the genes chosen were also present as single splice transcripts in the microarrays used. The reason for this selection criterion was to minimize discordance between the two gene expression profiling techniques as differences in probe designs between microarrays and Taq-Man assays might result in detection of additional splice variants. Finally, all of the TaqMan assays selected had suffixes of m1, which indicate that the probes were designed across splice junctions, and would avoid the detection of genomic DNA.

Expression levels of target genes were normalized to the geometric mean of three housekeeping genes, Sfrs9, Guk1 and Hnrpab. These genes were chosen as they were shown to be stable across the previously obtained microarray data. Eukaryotic 18S rRNA Endogenous Control was also tested together with the three housekeeping genes in preliminary experiments, and their stabilities were determined using the geNorm software. However, this gene was found to be the least stable of the four housekeeping genes tested and was thus further dropped as an endogenous control (data not shown).

Figure 12A:
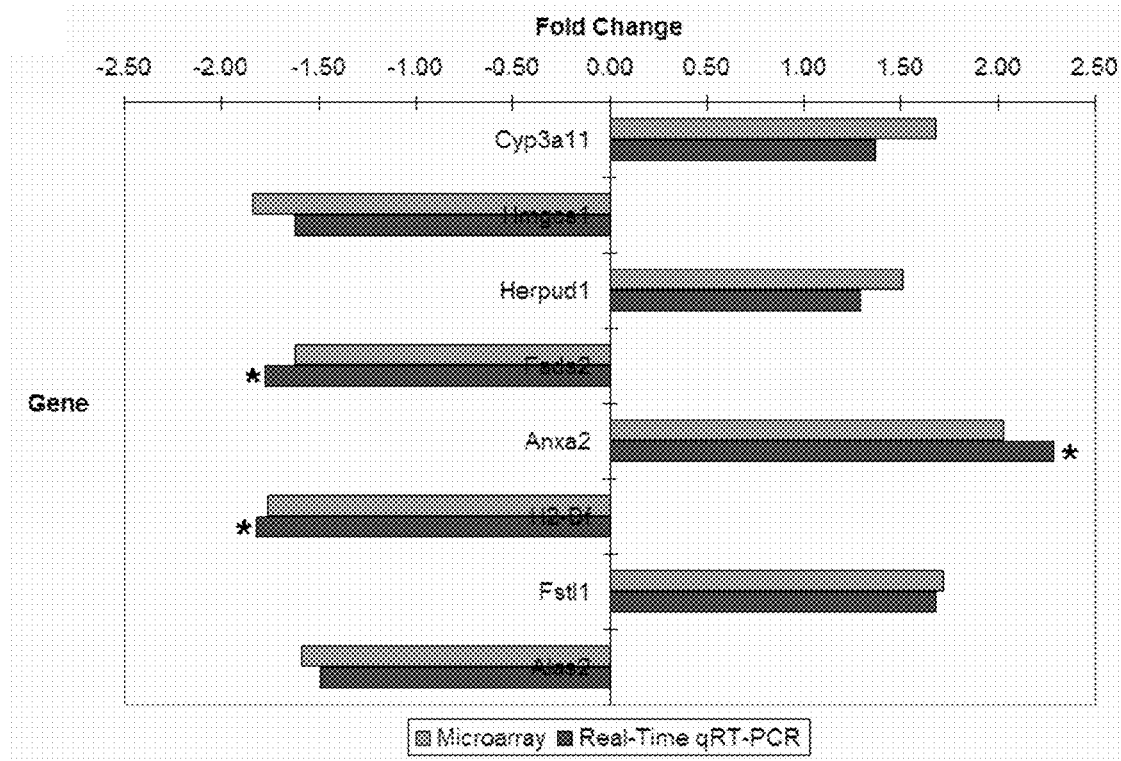
FIG. 12A is a diagram of the direction and magnitude of gene expression fold changes of eight target genes as determined by microarray and real-time qRT-PCR experiments and their correlation; the direction and magnitude of fold changes obtained from the real-time qRT-PCR technique were comparable to those obtained from the microarray technique. * $P<0.05$ for gene expression fold changes quantitated by real-time PCR experiments as determined by two-tailed unpaired Student's t-test.
Figure 12B:
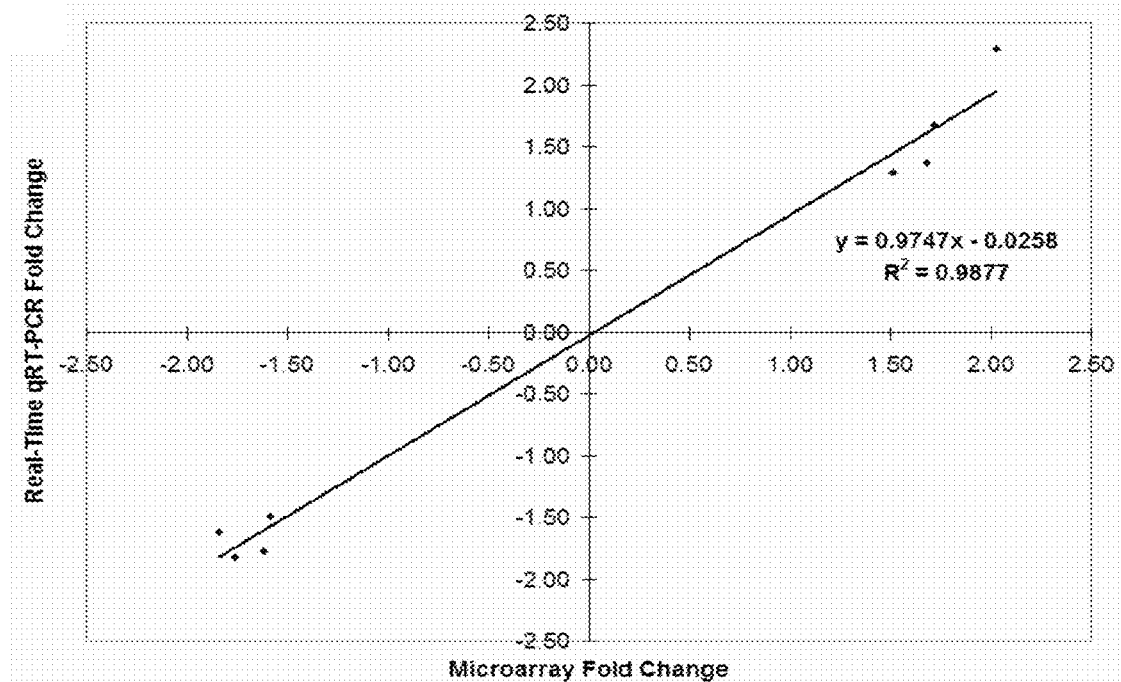
FIG. 12B presents a validation of the microarray data via real-time qrt-PCR and shows that correlation of fold changes obtained by these two gene expression profiling techniques was high with an $R^2=0.9877$.

Expression fold changes for each gene quantitated by the qBase software based on the real-time qRT-PCR data obtained, together with those determined by the previous microarray experiments, are shown in FIG. 12A. The direction and magnitude of fold changes obtained from the real-time qRT-PCR technique were comparable to those obtained from the microarray technique. As shown in FIG. 12B, correlation of fold changes obtained by the two gene expression profiling techniques was high ($R^2$=0.9877), thus validating the microarray data obtained.

Serum Cytokine Profiling Supported In Vivo Anti-Inflammatory Effects of Oil Palm Phenolics Multiplex cytokine profiling on serum samples was carried out using the Bio-Plex Suspension Array System (Bio-Rad Laboratories, Hercules, Calif.), which is a microbead and flow-based protein detection system based on the Luminex xMAP technology, available at the Medical Biotechnology Center, Faculty of Medicine, University of Malaya. The Bio-Plex Mouse Cytokine 23-Plex Cytokine Panel (Bio-Rad Laboratories, Hercules, Calif.), which included antibody-conjugated beads for 23 types of mouse cytokines, was also utilized. The cytokines present in this panel include IL-1α, IL-1β, IL-2, IL-3, IL-4, IL-5, IL-6, IL-9, IL-10, IL-12 (p40), IL-12 (p70), IL-13, IL-17, Eotaxin, G-CSF, GM-CSF, IFN-γ, KC, MCP-1 (MCAF), MIP-1α, MIP-1β, RANTES and TNF-α.

The experiment was carried out according to manufacturer's instructions. Each serum sample (n=6) was tested in duplicates. The data were analyzed using the Bio-Plex Manager Version 4.0 software (Bio-Rad Laboratories, Hercules, Calif.). Generation of standard curves, averaging of duplicate fluorescence readings of each serum sample, background subtraction with the blank and calculation of concentration for each cytokine were carried out by the Bio-Plex Manager software. The averaged concentration readings were exported into Microsoft Excel for statistical analysis, in which the two-tailed unpaired Student's t-test was used. Differences with t-test p-values of less than 0.05 were considered statistically significant.

Figure 13A:
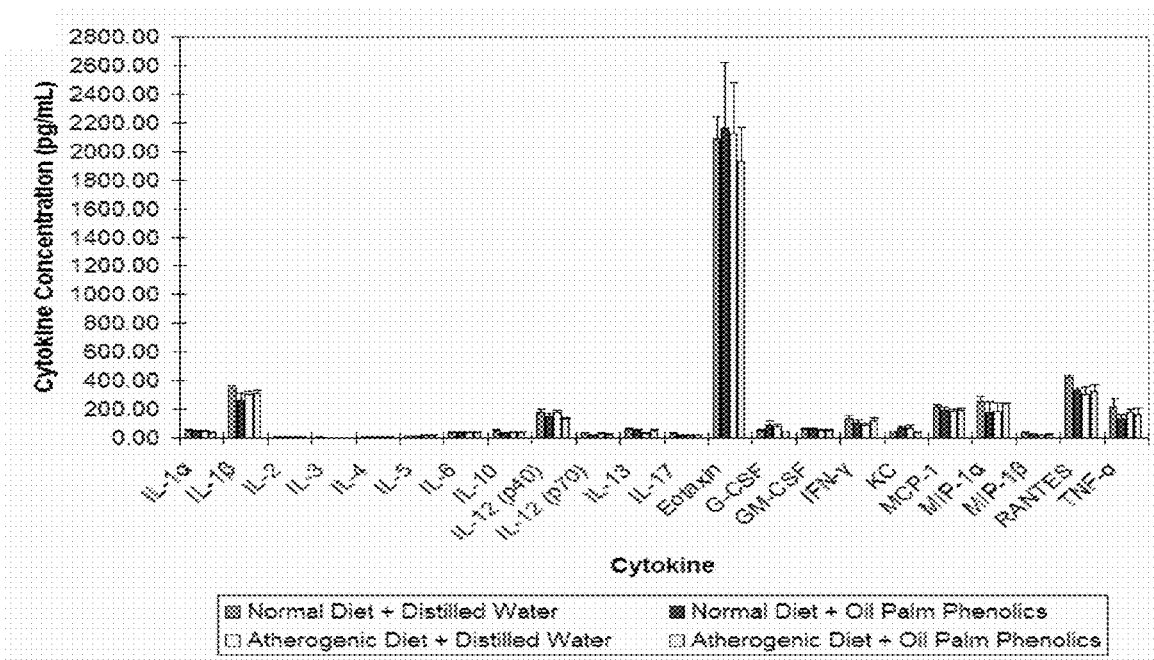
FIG. 13A diagrams results of cytokine profiling on blood serum samples from mice, based on the original Y-axis.
Figure 13B:
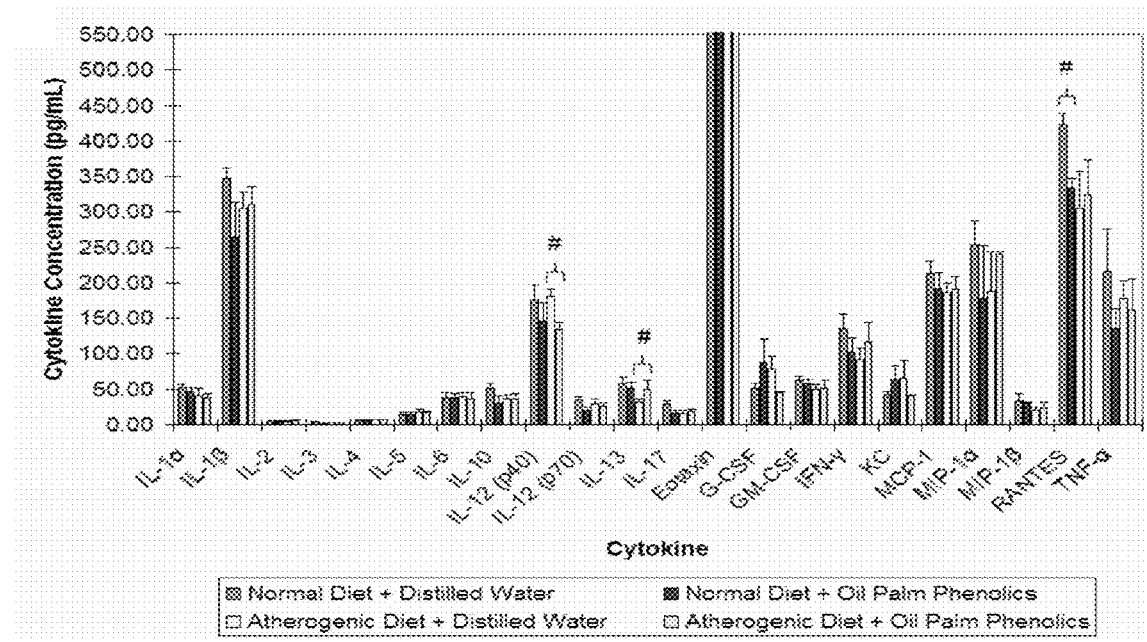
FIG. 13B diagrams results of cytokine profiling on blood samples from mice, based an adjusted Y-axis. # denotes those samples for which $p<0.05$; n=6. Error bars indicate S.E.M.
Figure 14A:
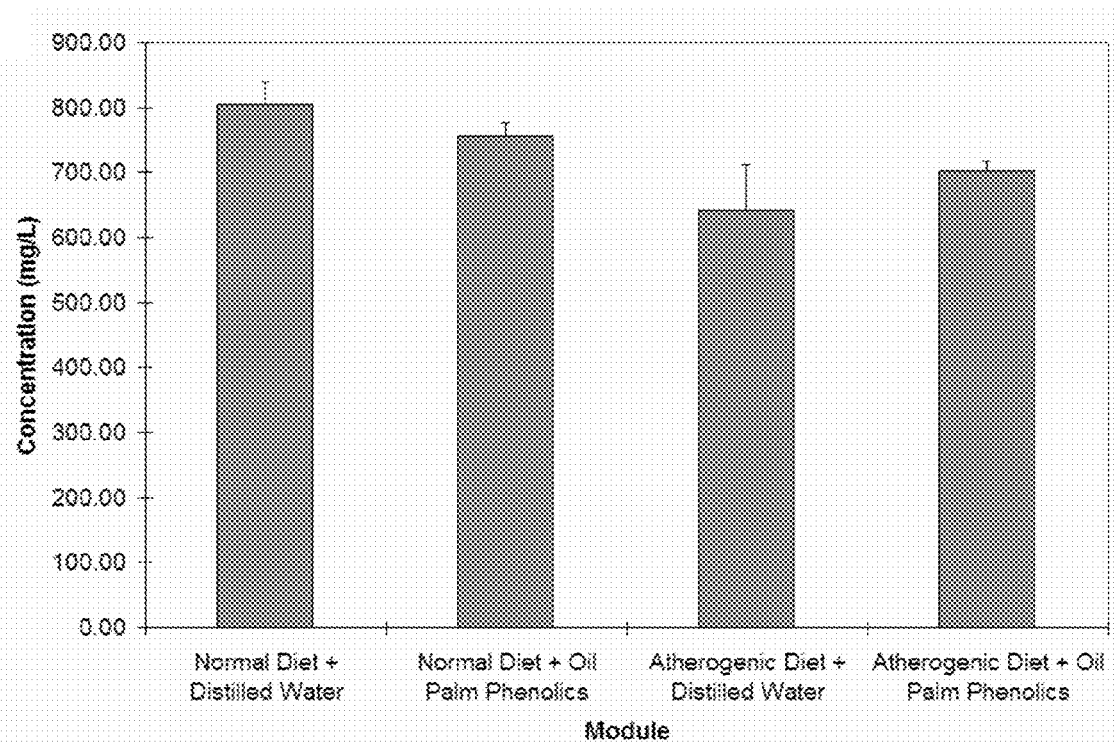
FIGS. 14A, 14B, 14C and 14D collectively diagram results of antioxidant analysis on blood serum samples from mice.
Figure 14B:
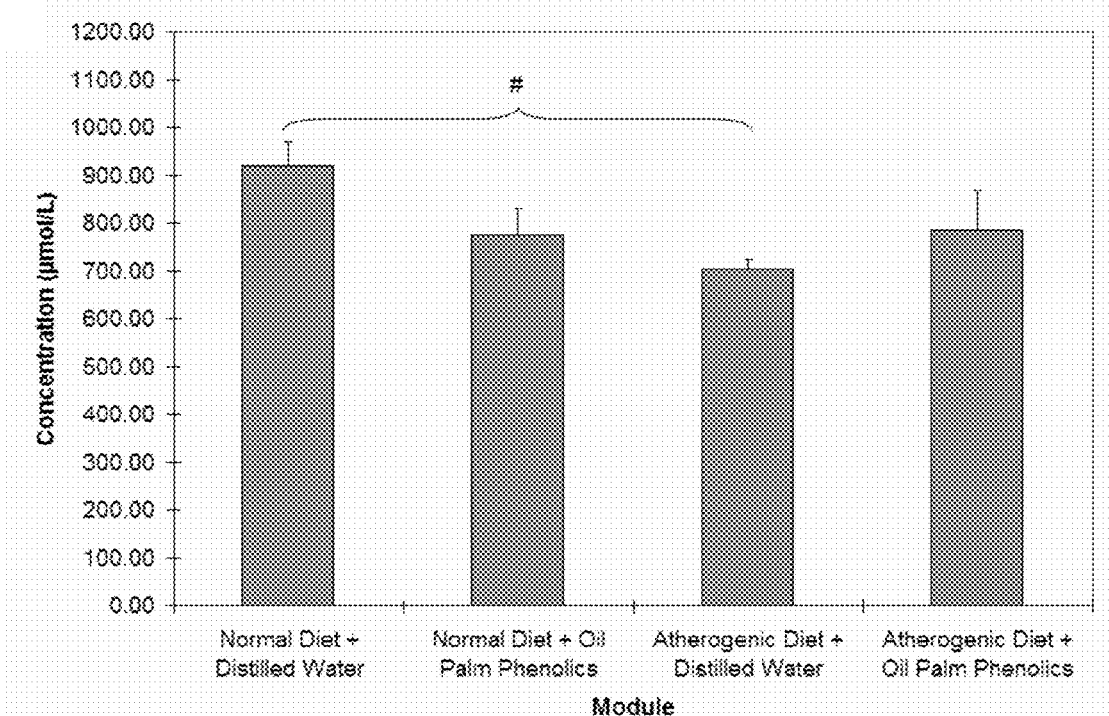
Figure 14C:
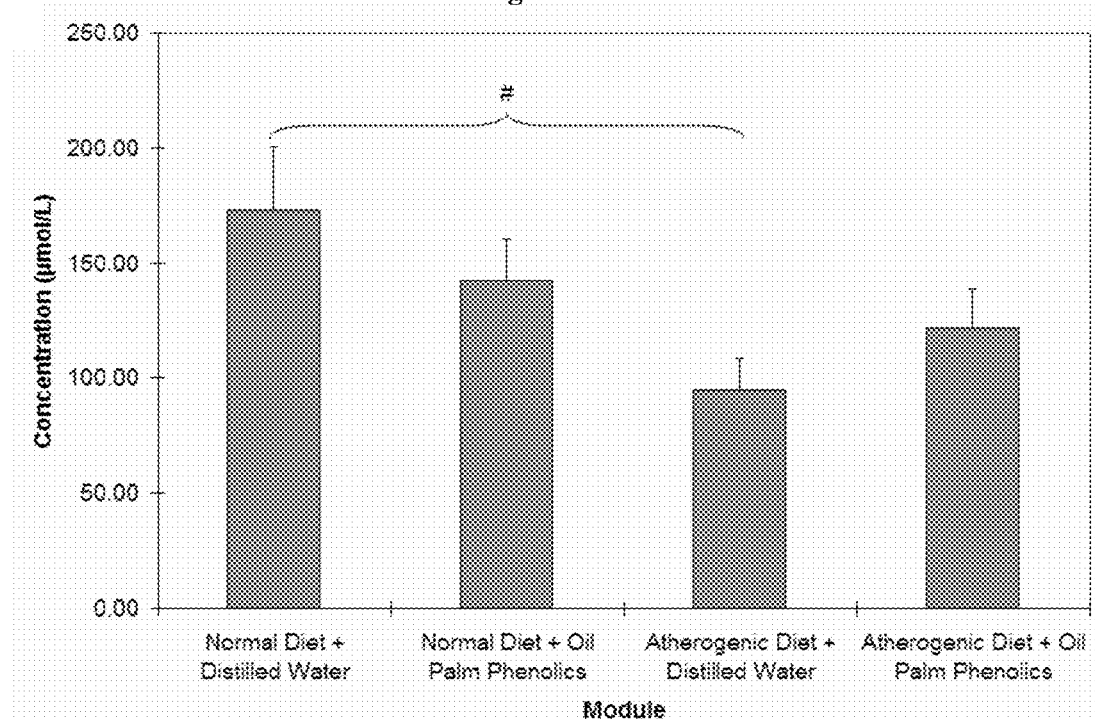
Figure 14D:
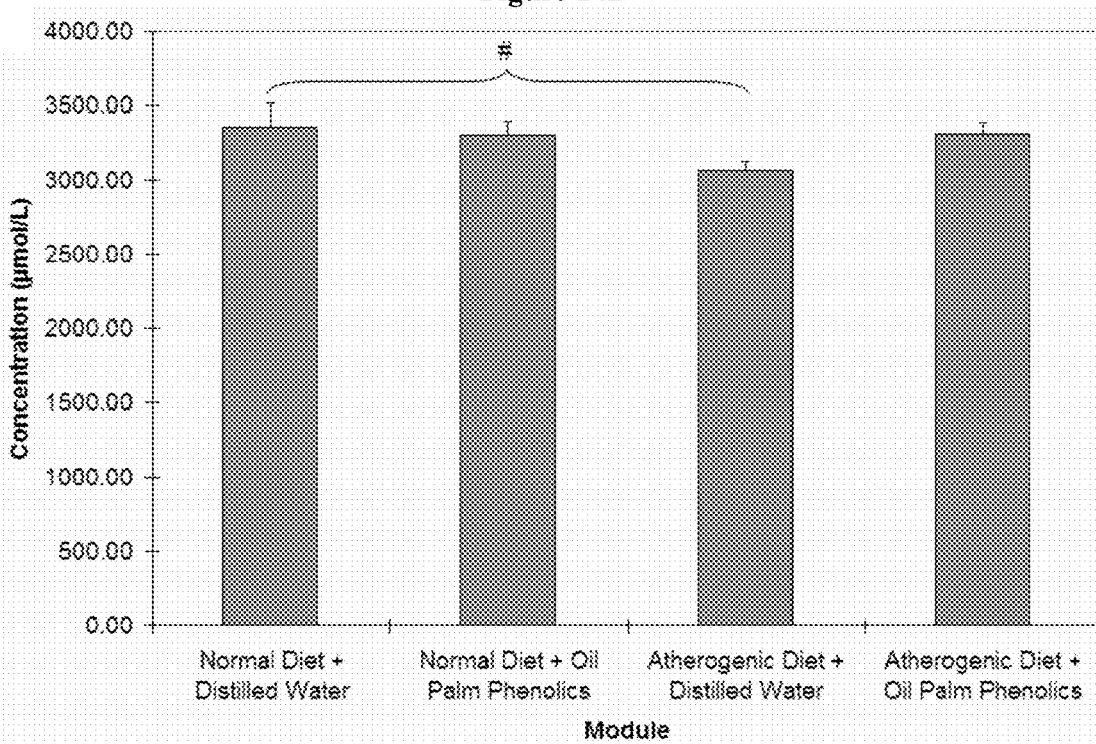

For serum cytokine profiling, the amounts of eotaxin were surprisingly high for all animals in the three groups (FIG. 13A). This may be caused by the exposure of the animals to the non-sterile environment as they were not maintained in a specific pathogen-free facility. In the normal diet module, RANTES was significantly reduced in the treatment group compared to the control group (FIG. 13B). This may be a sign of lowered inflammation as RANTES had been implied in inflammation, obesity and cerebral microvascular dysfunction. For those on the atherogenic diet, there was a significant decrease in interleukin-12 (p40 subunit) (IL-12 (p40)) and a significant increase in interleukin-13 (IL-13) in the group given oil palm phenolics when compared to the atherogenic control group (FIG. 13B).

As a component of the immune response, cytokines too play an important role in mediating the inflammatory response in atherosclerosis. Atherosclerotic lesions normally contain cytokines that promote a Th1 cellular immune response (interferon-γ, interleukin-1, interleukin-2, TNF-α and TNF-β) rather than a Th2 humoral immune response (interleukin-4, interleukin-5 and interleukin-10) [99]. In mice belonging to the atherogenic diet treatment group, a decrease in the pro-inflammatory IL-12 (p40) cytokine and an increase in the anti-inflammatory IL-13 cytokine in the sera were observed when compared to the atherogenic diet control group. This is believed to be an attenuation of the inflammatory response towards atherosclerosis.

IL-12 is a cytokine of innate immunity which is secreted by activated macrophages and dendritic cells, and is a key inducer of cell-mediated immunity as it stimulates the production of IFN-γ, stimulates the differentiation of CD4+ helper T lymphocytes into $T_H1$ cells as well as enhances cytolytic functions of activated NK cells and CD8+ cytolytic T lymphocytes. It has been implicated in atherosclerosis and other inflammatory diseases, and have been found to be attenuated by several antioxidative plant compounds such as catechins, curcumin, apigenin and silibinin. IL-13 is a cytokine of adaptive immunity which is secreted by CD4+ helper T lymphocytes ($T_H2$ cells), and it inhibits macrophages and antagonizes IFN-γ. The anti-inflammatory effects observed in the serum samples were consistent with the gene expression changes seen in the spleens of mice given oil palm phenolics, which indicate attenuation of the inflammatory response.

Serum Antioxidant Analysis Confirmed In Vivo Antioxidant Effects of Oil Palm Phenolics The basic mechanism for the antioxidant assays used in this study involves the transfer of an electron from the antioxidant to the probe, which is normally an oxidant. This results in the formation of an oxidized antioxidant and a reduced probe. Antioxidant analysis on serum samples was carried out using four assays including the total phenolics content by Folin-Ciocalteu reagent (TP-FCR) assay, the ferric reducing ability of plasma (FRAP) assay, the 2,2-diphenyl-1-picrylhydrazyl (DPPH) scavenging activity assay and the Trolox equivalent antioxidant capacity (TEAC) assay. All these assays were carried out using the Infinite M200 microplate reader (Tecan, Austria). Each serum sample (n=6) was tested in duplicates. Measurement settings and data acquisition were carried out using the Magellan Version 6.2 software (Tecan, Austria). Generation of standard curves, averaging of duplicate absorbance readings of each sample, background subtraction with the blank, calculation of concentration and statistical analysis for each assay were carried out in Microsoft Excel. Statistical analysis was carried out by using the two-tailed unpaired Student's t-test. Differences with t-test p-values of less than 0.05 were considered statistically significant.

For the TP-FCR assay, gallic acid was prepared in a range of 0 to 2000 mg/mL to generate the standard curve. For serum analysis, 15 µL of 100% ethanol was added to 15 µL of each serum sample in order to precipitate macromolecules out. The mixture was then vortexed for two minutes and centrifuged at 1100×g for five minutes. The clear supernatant was then collected for analysis. A master mix containing 40 µL of distilled water and 4 µL of Folin-Ciocalteu reagent for each reaction to be carried out was prepared. This master mix was then aliquoted into a clear 96-well flat bottom microplate. The microplate was read at an absorbance of 765 nm. 2 µL of sample or gallic acid standard diluent was then pipetted into each well, followed by 20 µL of 15% w/v disodium carbonate ($Na_2CO_3$). The microplate was then shaken at maximum intensity for 10 seconds and incubated at room temperature for 2 hours. Absorbance was read at 765 nm. The ΔA765 nm and concentration of gallic acid equivalent for each sample were calculated based on the standard curve obtained.

For the FRAP assay, ferrous sulphate heptahydrate ($FeSO_4.7H_2O$) was prepared in a range of 0 to 2000 µmol/L to generate the standard curve. Solutions A, B and C were then prepared. Solution A comprised of 300 mM acetate ($C_2H_3NaO_2.3H_2O$) buffer pH 3.6 in 16% v/v acetic acid ($C_2H_4O_2$). Solution B comprised of 10 mM 2,4,6,-tri(2-pyridyl)-s-triazine (TPTZ) solution in 40 mM hydrochloric acid (HCl). Solution C comprised of 20 mM ferric chloride hexahydrate ($FeCl_3.6H_2O$) solution in distilled water. The straw coloured FRAP reagent was then prepared by mixing 25 mL of Solution A, 2.5 mL of Solution B and 2.5 mL of Solution C. It was then kept in a water bath at 37° C. 180 µL of FRAP reagent was then aliquoted into a clear 96-well flat bottom microplate. The microplate was read at an absorbance of 593 nm. 18 µL of sample or $FeSO_4.7H_2O$ standard diluent was then pipetted into each well. The microplate was then shaken at maximum intensity for 10 seconds and incubated at 37° C. for 10 minutes. Absorbance was read at 593 nm. The ΔA593 nm and concentration of Trolox equivalent for each sample were calculated based on the standard curve obtained.

For the DPPH assay, Trolox was prepared in a range of 0 to 500 µmol/L to generate the standard curve. For serum samples, 15 µL of 100% ethanol was added to 15 µL of each serum sample in order to precipitate macromolecules out. The mixture was then vortexed for 2 minutes and centrifuged at 1100×g for 5 minutes. The clear supernatant was then collected for analysis. 0.2 mmol/L DPPH was prepared in 50% v/v ethanol. 95 µL of this DPPH solution was then aliquoted into a clear 96-well flat bottom microplate. The microplate was read at an absorbance of 515 nm. 5 µL of sample or Trolox standard diluent was then pipetted into each well. The microplate was then shaken at maximum intensity for 10 seconds and incubated at room temperature for 10 minutes. Absorbance was read at 515 nm. The ΔA515 nm and concentration of Trolox equivalent for each sample were calculated based on the standard curve obtained.

For the TEAC assay, a 7 mM 2,2'-azinobis(3-ethylbenzothiazoline-6-sulfonic acid (ABTS) solution and a 2.45 mM dipotassium persulfate ($K_2O_8S_2$) solution were first prepared in distilled water each. The ABTS reagent was then prepared by mixing 25 mL of ABTS solution with 12.5 mL of $K_2O_8S_2$ solution and held in darkness for 16 hours at room temperature to produce a dark green coloured solution. The following day, Trolox was prepared in a range of 0 to 200 µmol/L to generate the standard curve. 180 µL of ABTS reagent was then aliquoted into a clear 96-well flat bottom microplate. The microplate was read at an absorbance of 734 nm. 18 µL of sample or Trolox standard diluent was then pipetted into each well. The microplate was then shaken at maximum intensity for 10 seconds and incubated at 37° C. for 6 minutes. Absorbance was read at 734 nm. The ΔA734 nm and concentration of Trolox equivalent for each sample were calculated based on the standard curve obtained.

For serum antioxidant analysis, the standard curves obtained for the four assays carried out had $R^2$ values >0.9 (data not shown). No significant changes were caused by oil palm phenolics in the normal diet module (see FIGS. 14A-14D), and this was quite unexpected. However, it should be noted that the administration of a commercially available source of olive phenolics (Olivenol Livin') derived from olive mill wastewater also did not increase plasma total antioxidant status although blood was drawn one hour after ingestion of the preparation for analysis, similar to previous studies carried out on olive oil wastewater extract and olive leaf supplements. The lack of effect on the total antioxidant capacity observed was interpreted in terms of lower attainable concentrations of olive phenolics as compared to endogenous antioxidants. This may also be the case for oil palm phenolics.

The antioxidant analysis carried out on the serum samples showed that for the atherogenic diet control group, there was a significant decrease in antioxidant capacity when compared to mice given the normal diet, which indicates a higher oxidative stress in mice given the atherogenic diet (see FIGS. 14A-14D). This is similar to the observations carried out by previous studies. The atherogenic diet treatment group on the other hand, showed almost similar antioxidant capacity when compared to mice given the normal diet, thus indicating that the antioxidant resistance of mice supplemented with oil palm phenolics was still high although they were also given the atherogenic diet. This further implies that oil palm phenolics restored the antioxidant capacity of mice given the atherogenic diet, and is in line with the gene expression changes observed in the major organs of mice, in which antioxidant genes were up-regulated.

As a summary, it was found that oil palm phenolics up-regulated fatty acid beta oxidation and down-regulated cholesterol biosynthesis in livers of mice given the normal diet. This might explain the slight delay in weight gain caused by the extract, and further imply the application of oil palm phenolics in promoting weight loss and preventing obesity. The administration of the atherogenic diet increased cellular proliferation and turnover in the major organs of mice studied, including the liver, spleen and heart. An increased intake of fat and cholesterol caused an increased circulation and utilization of the respective metabolites in these organs, which further induced oxidative stress, inflammation, injury, cellular proliferation and tissue regeneration to compensate for the increased metabolic burden, especially in the liver. Among the genes found to be regulated by the atherogenic diet, it was most apparent that those linked to the pro-inflammatory Tnfa were up-regulated, while those linked to the anti-inflammatory Tgfb were down-regulated, especially in the spleen and heart.

On the other hand, oil palm phenolics showed signs of attenuating the effects of the atherogenic diet. This extract increased unfolded protein response in livers of mice, which is important in getting rid of misfolded proteins, while attenuated antigen presentation and processing in spleens of mice, similar to the effects of statins. Oil palm phenolics also increased the expression of antioxidant genes in the hearts of these mice. A majority (>50%) of the genes regulated by oil palm phenolics in the different organs showed a difference in the direction of regulation when compared to the atherogenic diet.

Despite that fact that oil palm phenolics did not significantly alter the body and liver weights as well as the clinical biochemistry and hematology parameters of mice on the atherogenic diet, further cytokine profiling and antioxidant analysis on mouse blood serum samples managed to confirm the in vivo anti-inflammatory and antioxidant effects of the extract. In contrast with the effects of oil palm phenolics which down-regulated cholesterol biosynthesis genes in mice fed the normal diet, the extract did not cause a further reduction in this group of genes. This made sense as administration of the atherogenic diet already down-regulated cholesterol biosynthesis, and thus further down-regulation of the pathway would be futile to prevent atherosclerosis. On the other hand, oil palm phenolics acted as an anti-inflammatory agent and an antioxidant in mice given the atherogenic diet to prevent oxidative stress caused by the diet. These findings suggest that oil palm phenolics can be used to overcome the effects of an atherogenic diet and further imply the potential of this extract as a chemopreventive agent for atherosclerosis and cardiovascular disease.

Generally, the composition in accordance with the present invention may be prepared in various suitable forms for direct or oral administration for the health purposes as discussed earlier in the preceding sections.

For instance, the compositions of the present invention may be provided in the following forms, but no limiting to, suitable for oral administration containing a pre-determined amount of the extract; a solution or a suspension in an aqueous or non-aqueous liquid, tablets, capsules and the likes.

The compositions of the invention may also be administered to a human in a dietary supplement form. Dietary supplements incorporating the active composition can be prepared by adding the composition to a food in the process of preparing the food. The composition is added to the food in an amount selected to deliver a desired dose of the composition to the consumer of the food.

The composition comprising the compounds in accordance with the present invention may be prepared for use in a pharmaceutically effective or nutraceutically effective amount, solely on its own or in combination with other agents or compounds deemed appropriate by a person skilled in the art.

In one embodiment the compositions may be administered in form of doses, within a predetermined period of time, whereby it may be administered for example but not limiting to daily, weekly or monthly.

In another embodiment the compositions may be provided in conventional treatment forms, pharmaceutical formulations or as nutritional supplement.

In one embodiment the composition of the present invention may be provided in a nutraceutical form.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. A method for treating obesity and reducing cholesterol biosynthesis in a patient in need thereof, said method comprising
administering to said patient a pharmaceutically acceptable amount of a composition comprising water-soluble oil palm phenolics extracted from a palm oil mill effluent using a solvent-free process, wherein an antioxidant content of the oil palm phenolics is about 1500 ppm gallic acid equivalent; and wherein the antioxidant content of the oil palm phenolics up-regulates fatty acid beta oxidation genes, and wherein the antioxidant content of the oil palm phenolics down regulates cholesterol biosynthesis genes.

2. The method of claim 1, wherein the composition is provided in solid dosage form.

3. The method of claim 1, wherein the composition is provided in liquid dosage form.

4. The method of claim 1, wherein the composition is provided in solution form.

5. The method of claim 1, wherein the composition is provided in a pharmaceutically effective form.

6. The method of claim 1, wherein the composition is provided in nutraceutical form.

7. The method of claim 1, wherein the composition is in nutritional supplementary form.

8. The method of claim 1, wherein the composition is provided in a form suitable for oral administration.

9. The method of claim 1, wherein fatty acid beta oxidation genes are those encoding sterol carrier protein (Scp), lysophospholipase (Lypla1), monoglyceride lipase (Mgll), acetyl-coA dehydrogenase (Acadl), acyl-coA dehydrogenases (Acads, Acad8), hydroxyacyl-coA dehydrogenases (Hadhb, Hadhsc), acetyl-coA acetyltransferases (Acat2, Acat3) and acetyl-coA acyltransferase (Acaa2).

10. The method of claim 1, wherein the cholesterol biosynthesis genes are those encoding lanosterol synthase (Lss), sterol-C4-methyl oxidase-like (Sc4 mol), farnesyl diphosphate synthetase (Fdps), NAD(P) dependent steroid dehydrogenase-like (Nsdhl) and 3-hydroxy-3-methylglutaryl-Coenzyme A synthase 1 (Hmgcll).

\* \* \* \* \*